United States Patent
Nierzwick et al.

(10) Patent No.: US 8,687,811 B2
(45) Date of Patent: *Apr. 1, 2014

(54) DIABETES CARE KIT THAT IS PRECONFIGURED TO ESTABLISH A SECURE BIDIRECTIONAL COMMUNICATION LINK BETWEEN A BLOOD GLUCOSE METER AND INSULIN PUMP

(71) Applicant: Roche Diagnostics Operations, Inc., Indianapolis, IN (US)

(72) Inventors: Mark Nierzwick, Brownsburg, IN (US); Phillip E. Pash, Indianapolis, IN (US); James Duane Tenbarge, Fishers, IN (US)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/741,587

(22) Filed: Jan. 15, 2013

(65) Prior Publication Data

US 2013/0131631 A1      May 23, 2013

Related U.S. Application Data

(63) Continuation of application No. 12/975,473, filed on Dec. 22, 2010, now Pat. No. 8,401,194.

(60) Provisional application No. 61/393,562, filed on Oct. 15, 2010.

(51) Int. Cl.
   *H04L 29/06* (2006.01)

(52) U.S. Cl.
   USPC .......................... 380/270; 380/255; 380/278

(58) Field of Classification Search
   USPC ............ 380/255, 270, 278; 604/66, 151, 264
   See application file for complete search history.

(56) References Cited

U.S. PATENT DOCUMENTS

| 6,424,847 | B1 | 7/2002 | Mastrototaro et al. |
| 6,895,263 | B2 | 5/2005 | Shin et al. |
| 6,931,327 | B2 | 8/2005 | Goode, Jr. et al. |

(Continued)

FOREIGN PATENT DOCUMENTS

| WO | WO 03071930 | 9/2003 |
| WO | WO 2008154467 | 12/2008 |
| WO | WO2010111505 | 9/2010 |

OTHER PUBLICATIONS

Malasri et al., "Securing Wireless Implantable Devices for Healthcare: Ideas and Challenges", IEEE Communications Magazine, vol. 47, No. 7 (Jul. 2009).

(Continued)

*Primary Examiner* — Hadi Armouche
*Assistant Examiner* — Dao Ho
(74) *Attorney, Agent, or Firm* — Harness, Dickey

(57) ABSTRACT

A diabetes care kit for providing diagnostics and therapy that is preconfigured to reduce initial setup by a user. The kit can include a handheld diabetes managing device and insulin pump. The handheld diabetes managing device and insulin pump can each be preloaded with an encryption key such that the handheld diabetes managing device and the insulin pump are paired and a secure bidirectional communication link exists between the handheld diabetes managing device and the insulin pump.

10 Claims, 15 Drawing Sheets

(56) References Cited

U.S. PATENT DOCUMENTS

| | | |
|---|---|---|
| 7,003,341 B2 | 2/2006 | Say et al. |
| 7,029,444 B2 | 4/2006 | Shin et al. |
| 7,098,803 B2 | 8/2006 | Mann et al. |
| 7,190,988 B2 | 3/2007 | Say et al. |
| 7,276,029 B2 | 10/2007 | Goode, Jr. et al. |
| 7,599,726 B2 | 10/2009 | Goode, Jr. et al. |
| 7,797,028 B2 | 9/2010 | Goode, Jr. et al. |
| 7,826,382 B2 | 11/2010 | Sicurello et al. |
| 2002/0193679 A1* | 12/2002 | Malave et al. ............ 600/407 |
| 2007/0055799 A1* | 3/2007 | Koehler et al. ............ 710/62 |
| 2007/0255125 A1 | 11/2007 | Moberg et al. |
| 2008/0097908 A1* | 4/2008 | Dicks et al. ............ 705/50 |
| 2008/0119708 A1 | 5/2008 | Budiman |
| 2008/0312512 A1 | 12/2008 | Brukalo et al. |
| 2008/0312584 A1 | 12/2008 | Montgomery et al. |
| 2008/0312585 A1 | 12/2008 | Brukalo et al. |
| 2009/0149803 A1 | 6/2009 | Estes et al. |
| 2009/0254037 A1 | 10/2009 | Bryant et al. |
| 2010/0115279 A1 | 5/2010 | Frikart et al. |
| 2010/0305421 A1 | 12/2010 | Ow-Wing |
| 2012/0093311 A1 | 4/2012 | Nierzwick et al. |
| 2012/0095393 A1 | 4/2012 | Reinke et al. |

OTHER PUBLICATIONS

Sye Loong Keoh et al., "Securing Body Sensor Networks: Sensor Association and Key Management", Pervasive Computing and Communications (2009).

Bluetooth SIG, "Bluetooth User Interface", www.bluetooth.orq/Technical_Specifications/whitepapers.htm (Sep. 13, 2007).

Cagalj et al., "Key Agreement in Peer-to-Peer Wireless Networks", Proceedings of the IEEE, IEEE New York, US; vol. 94, No. 2 (Feb. 1, 2006).

Xiao et al., "A Survey of Key Management Schemes in Wireless Sensor Networks", Computer Communications, Elsevier Science Publishers BV, Amsterdam, NL, vol. 30, Nos. 11-12 (Aug. 24, 2007).

* cited by examiner

DIABETES CARE KIT THAT IS PRECONFIGURED TO ESTABLISH A SECURE BIDIRECTIONAL COMMUNICATION LINK BETWEEN A BLOOD GLUCOSE METER AND INSULIN PUMP

CROSS-REFERENCE TO RELATED APPLICATIONS

This application is a continuation application of U.S. patent application Ser. No. 12/975,473, filed Dec. 22, 2010, which claims the benefit of U.S. Provisional Application No. 61/393,562, filed on Oct. 15, 2010. The entire disclosures of the above applications are incorporated herein by reference.

FIELD

The present disclosure relates generally to medical devices and more particularly to a simplified process for pairing a blood glucose meter and an insulin pump for secure and reliable wireless communication.

BACKGROUND

Medical devices are often used as diagnostic devices and/or therapeutic devices in diagnosing and/or treating medical conditions of patients. For example, a blood glucose meter is used as a diagnostic device to measure blood glucose levels of patients suffering from diabetes. An insulin infusion pump is used as a therapeutic device to administer insulin to patients suffering from diabetes.

Diabetes mellitus, often referred to as diabetes, is a chronic condition in which a person has elevated blood glucose levels that result from defects in the body's ability to produce and/or use insulin. There are three main types of diabetes. Type 1 diabetes can be autoimmune, genetic, and/or environmental and usually strikes children and young adults. Type 2 diabetes accounts for 90-95% of diabetes cases and is linked to obesity and physical inactivity. Gestational diabetes is a form of glucose intolerance diagnosed during pregnancy and usually resolves spontaneously after delivery.

In 2009, according to the World Health Organization, at least 220 million people worldwide suffer from diabetes. In 2005, an estimated 1.1 million people died from diabetes. The incidence of diabetes is increasing rapidly, and it is estimated that between 2005 and 2030, the number of deaths from diabetes will double. In the United States, nearly 24 million Americans have diabetes, and an estimated 25% of seniors age 60 and older are affected. The Centers for Disease Control and Prevention forecast that 1 in 3 Americans born after 2000 will develop diabetes during their lifetime. The National Diabetes Information Clearinghouse estimates that diabetes costs $132 billion in the United States alone every year. Without treatment, diabetes can lead to severe complications such as heart disease, stroke, blindness, kidney failure, amputations, and death related to pneumonia and flu.

Diabetes is managed primarily by controlling the level of glucose in the bloodstream. This level is dynamic and complex, and is affected by multiple factors including the amount and type of food consumed, and the amount of insulin (which mediates transport of glucose across cell membranes) in the blood. Blood glucose levels are also sensitive to exercise, sleep, stress, smoking, travel, illness, menses, and other psychological and lifestyle factors unique to individual patients. The dynamic nature of blood glucose and insulin, and all other factors affecting blood glucose, often require a person with diabetes to forecast blood glucose levels. Therefore, therapy in the form of insulin or oral medications, or both, can be timed to maintain blood glucose levels in an appropriate range.

Management of diabetes is time-consuming for patients because of the need to consistently obtain reliable diagnostic information, follow prescribed therapy, and manage lifestyle on a daily basis. Diagnostic information, such blood glucose, is typically obtained from a capillary blood sample with a lancing device and is then measured with a handheld blood glucose meter. Interstitial glucose levels may be obtained from a continuous glucose sensor worn on the body. Prescribed therapies may include insulin, oral medications, or both. Insulin can be delivered with a syringe, an ambulatory infusion pump, or a combination of both. With insulin therapy, determining the amount of insulin to be injected can require forecasting meal composition of fat, carbohydrates and proteins along with effects of exercise or other physiologic states. The management of lifestyle factors such as body weight, diet, and exercise can significantly influence the type and effectiveness of a therapy.

Management of diabetes involves large amounts of diagnostic data and prescriptive data acquired in a variety of ways: from medical devices, from personal healthcare devices, from patient-recorded logs, from laboratory tests, and from healthcare professional recommendations. Medical devices include patient-owned bG meters, continuous glucose monitors, ambulatory insulin infusion pumps, diabetes analysis software, and diabetes device configuration software. Each of these systems generates and/or manages large amounts of diagnostic and prescriptive data. Personal healthcare devices include weight scales, blood pressure cuffs, exercise machines, thermometers, and weight management software. Patient recorded logs include information relating to meals, exercise and lifestyle. Lab test results include HbA1C, cholesterol, triglycerides, and glucose tolerance. Healthcare professional recommendations include prescriptions, diets, test plans, and other information relating to the patient's treatment.

There is a need for a handheld device to aggregate, manipulate, manage, present, and communicate diagnostic data and prescriptive data from medical devices, personal healthcare devices, patient recorded information, biomarker information, and recorded information in an efficient manner. The handheld device can improve the care and health of a person with diabetes so that the person with diabetes can lead a full life and reduce the risk of complications from diabetes.

Additionally, to effectively manage the care and health of the patient, there is a need for the handheld device to communicate with other medical devices and systems. In order to communicate securely and reliably, the handheld device may need to establish a secure communication link between itself and the other medical devices and systems. Such a process may require a user (such as a patient with reduced visual acuity and/or technical skill) to follow a complex procedure that requires extensive user input. Accordingly, there is a need for a method of establishing a secure communication link between the handheld device and other medical devices/systems that is relatively simple and reduces the number and complexity of user inputs. Further, there is a need for a diabetes management system that reduces the number and complexity of user inputs to utilize and establish a secure communication link between various devices.

The background description provided herein is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

SUMMARY

According to the present disclosure, a diabetes care kit for providing diagnostics and therapy that is preconfigured to reduce initial setup by a user is presented. The kit can include a handheld diabetes managing device and insulin pump. The handheld diabetes managing device and the insulin pump can be paired such that a secure bidirectional communication link exists between the handheld diabetes managing device and the insulin pump. The handheld diabetes managing device can include a blood glucose meter, a first processor, a first memory, a first communication module and a first antenna. The blood glucose meter can be configured to determine a blood glucose level of a user. The first processor can be coupled to the blood glucose meter. Additionally, the first processor can be configured to generate an insulin pump command based on the blood glucose level. The first memory can be coupled to the processor and can be preloaded with an encryption key. The first communication module can coupled to the processor and first memory. Further, the first communication module can be configured to generate an encrypted communication message based on the insulin pump command and the encryption key. The first antenna can be coupled to the first communication module. The first antenna can also be configured to transmit the encrypted communication message.

The insulin pump can include an insulin dosing module, a second processor, a second memory, a second communication module and a second antenna. The insulin dosing module can be configured to dispense insulin based on an insulin dose command. The second processor can be coupled to the insulin dosing module. Further, the second processor can be configured to generate the insulin dose command based on the insulin pump command. The second memory can be coupled to the second processor and preloaded with the encryption key. The second communication module can be coupled to the second processor and the second memory. Additionally, the second communication module can be configured to decode the encrypted communication message based on the encryption key to obtain the insulin pump command. The second antenna can be coupled to the second communication module. The second antenna can also be configured to receive the encrypted communication message.

According to the present disclosure, a method of manufacturing a diabetes care kit for providing diagnostics and therapy that is preconfigured to reduce initial setup by a user is presented. The method can include providing a handheld diabetes managing device, providing an insulin pump, loading an encryption key in the handheld diabetes managing device and insulin pump and establishing a secure bidirectional communication link between the handheld diabetes managing device and the insulin pump by pairing the handheld diabetes managing device with the insulin pump. The handheld diabetes managing device can include a blood glucose meter configured to determine a blood glucose level of a patient, a first processor coupled to the blood glucose meter and configured to generate an insulin pump command based on the blood glucose level, a first memory coupled to the first processor, a first communication module coupled to the first processor and first memory and configured to generate an encrypted communication message based on the insulin pump command, and a first antenna coupled to the first communication module and configured to transmit the encrypted communication message. The insulin pump can include an insulin dosing module configured to dispense insulin to the patient based on an insulin dose command, a second processor coupled to the insulin dosing module and configured to generate the insulin dose command based on the insulin pump command, a second memory coupled to the second processor, a second communication module coupled to the second processor and the second memory and configured to decode the encrypted communication message to obtain the insulin pump command, and a second antenna coupled to the second communication module and configured to receive the encrypted communication message. The encryption key can be loaded in the first and second memory and be utilized to generate the encrypted communication message at the handheld diabetes managing device and to decode the encrypted communication message at the insulin pump.

Further areas of applicability of the present disclosure will become apparent from the detailed description provided hereinafter. It should be understood that the detailed description and specific examples are intended for purposes of illustration only and are not intended to limit the scope of the disclosure.

BRIEF DESCRIPTION OF THE DRAWINGS

The present disclosure will become more fully understood from the detailed description and the accompanying drawings, wherein.

DETAILED DESCRIPTION

Figure 1:
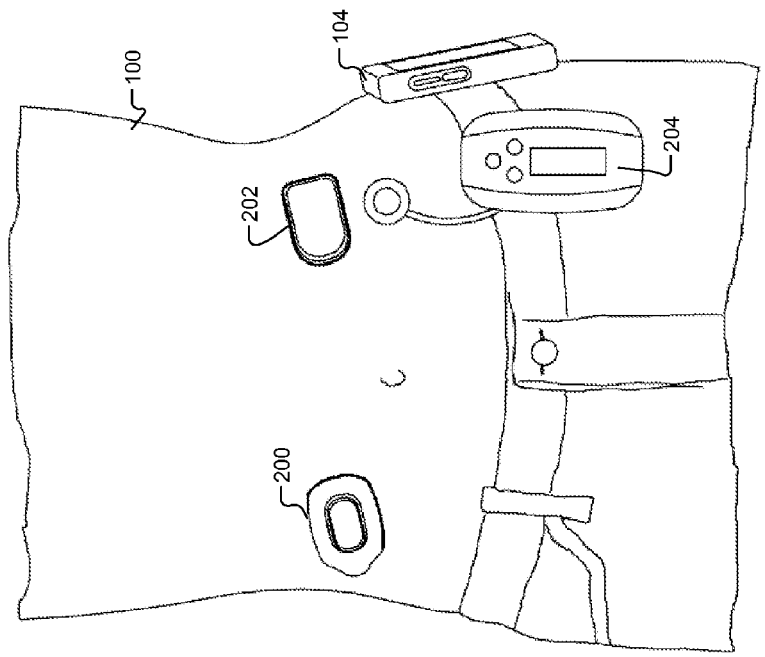
FIG. 1 shows a patient and a treating clinician.

Referring now to FIG. 1, a person 100 with diabetes and a healthcare professional 102 are shown in a clinical environment. Persons with diabetes include persons with metabolic syndrome, pre-diabetes, type 1 diabetics, type 2 diabetics, and gestational diabetics and are collectively referred to as a patient. Healthcare providers for diabetes are diverse and include nurses, nurse practitioners, physicians, and endocrinologists and are collectively referred to as a clinician.

During a healthcare consultation, the patient 100 typically shares with the clinician 102 a variety of patient data including blood glucose measurements, continuous glucose monitor data, amounts of insulin infused, amounts of food and beverages consumed, exercise schedules, and other lifestyle information. The clinician 102 can obtain additional patient data that includes measurements of HbA1C, cholesterol levels, triglycerides, blood pressure, and weight of the patient 100. The patient data can be recorded manually or electronically on a handheld diabetes management device 104, a diabetes analysis software executed on a personal computer (PC) 106, and/or a web-based diabetes analysis site (not shown). The clinician 102 can analyze the patient data manually or electronically using the diabetes analysis software and/or the web-based diabetes analysis site. After analyzing the patient data and reviewing adherence of the patient 100 to previously prescribed therapy, the clinician 102 can decide whether to modify the therapy for the patient 100.

Figure 2:
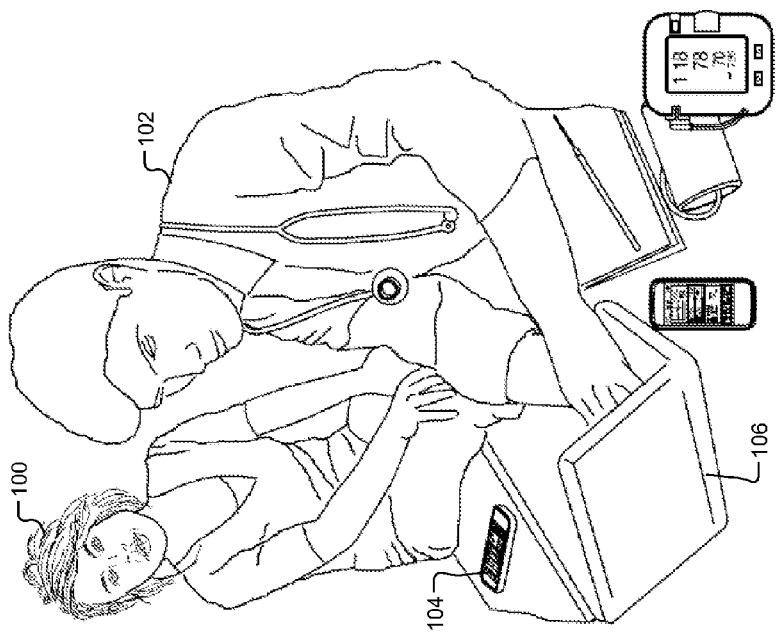
FIG. 2 shows a patient with a continuous glucose monitor (CGM), ambulatory durable insulin infusion pump, ambulatory non-durable insulin infusion pump, and diabetes manger.

Referring now to FIG. 2, the patient 100 can use a continuous glucose monitor (CGM) 200, an ambulatory durable insulin infusion pump 202 or an ambulatory non-durable insulin infusion pump 204 (collectively insulin pump 202 or 204), and the handheld diabetes management device 104 (hereinafter the diabetes manager 104). The CGM 200 uses a subcutaneous sensor to sense and monitor the amount of glucose in the blood of the patient 100 and communicates corresponding readings to the handheld diabetes management device 104.

The diabetes manager 104 performs various tasks including measuring and recording blood glucose levels, determining an amount of insulin to be administered to the patient 100 via the insulin pump 202 or 204, receiving patient data via a user interface, archiving the patient data, etc. The diabetes manager 104 periodically receives readings from the CGM 200 indicating insulin level in the blood of the patient 100. The diabetes manager 104 transmits instructions to the insulin pump 202 or 204, which delivers insulin to the patient 100. Insulin can be delivered in the form of a bolus dose, which raises the amount of insulin in the blood of the patient 100 by a predetermined amount. Additionally, insulin can be delivered in a scheduled manner in the form of a basal dose, which maintains a predetermined insulin level in the blood of the patient 100.

Figure 3:
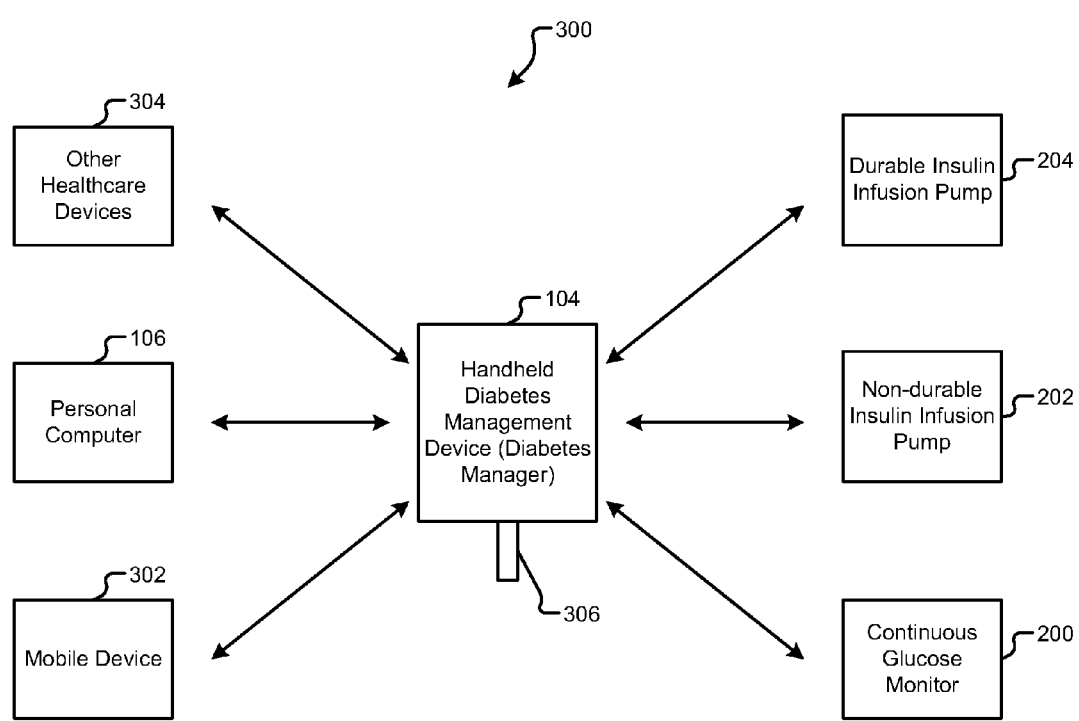
FIG. 3 shows a diabetes care system of systems used by patients and clinicians to manage diabetes.

Referring now to FIG. 3, a diabetes management system 300 used by the patient 100 and the clinician 102 includes one or more of the following devices: the diabetes manager 104, the continuous glucose monitor (CGM) 200, the insulin pump 202 or 204, a mobile device 302, the diabetes analysis software on the PC 106, and other healthcare devices 304. The diabetes manager 104 is configured as a system hub and communicates with the devices of the diabetes management system 300. Alternatively, the insulin pump 204 or the mobile device 302 can serve as the system hub. Communication between the various devices in the diabetes management system 300 can be performed using wireless interfaces (e.g., Bluetooth) and/or wireline interfaces (e.g., USB). Communication protocols used by these devices can include protocols compliant with the IEEE 11073 standard as extended using guidelines provided by Continua® Health Alliance Design Guidelines. Further, healthcare records systems such as Microsoft® HealthVault™ and Google™ Health can be used by the patient 100 and clinician 102 to exchange information.

The diabetes manager 104 can receive blood glucose readings from one or more sources (e.g., from the CGM 200). The CGM 200 continuously measures the blood glucose level of the patient 100. The CGM 200 periodically communicates the blood glucose level to the diabetes manager 104. The diabetes manager 104 and the CGM 200 communicate wirelessly using a proprietary Gazell wireless protocol developed by Nordic Semiconductor, Inc. or any other wireless protocol (Bluetooth Low Energy, etc.).

Additionally, the diabetes manager 104 includes a blood glucose meter (BGM) and a port that communicates with the BGM (both not shown). The port can receive a blood glucose measurement strip 306. The patient 100 deposits a sample of blood or other bodily fluid on the blood glucose measurement strip 306. The BGM analyzes the sample and measures the blood glucose level in the sample. The blood glucose level measured from the sample and/or the blood glucose level read by the CGM 200 can be used to determine the amount of insulin to be administered to the patient 100.

The diabetes manager 104 communicates with the insulin pump 202 or 204. The insulin pump 202 or 204 can be configured to receive instructions from the diabetes manager 104 to deliver a predetermined amount of insulin to the patient 100. Additionally, the insulin pump 202 or 204 can receive other information including meal and/or exercise schedules of the patient 100. The insulin pump 202 or 204 can determine the amount of insulin to administer based on the additional information.

The insulin pump 202 or 204 can also communicate data to the diabetes manager 104. The data can include amounts of insulin delivered to the patient 100, corresponding times of delivery, and pump status. The diabetes manager 104 and the insulin pump 202 or 204 can communicate using a wireless communication protocol such as Bluetooth. Other wireless or wireline communication protocols can also be used.

In addition, the diabetes manager 104 can communicate with other healthcare devices 304. For example, the other healthcare devices 304 can include a blood pressure meter, a weight scale, a pedometer, a fingertip pulse oximeter, a thermometer, etc. The other healthcare devices 304 obtain and communicate personal health information of the patient 100 to the diabetes manager 104 through wireless, USB, or other interfaces. The other healthcare devices 304 use communication protocols compliant with ISO/IEEE 11073 extended using guidelines from Continual® Health Alliance. The diabetes manager 104 can communicate with the other healthcare devices 304 using interfaces including Bluetooth, USB, etc. Further, the devices of the diabetes management system 300 can communicate with each other via the diabetes manager 104.

The diabetes manager 104 can communicate with the PC 106 using Bluetooth, USB, or other interfaces. A diabetes management software running on the PC 106 includes an analyzer-configurator that stores configuration information of the devices of the diabetes management system 300. The configurator has a database to store configuration information of the diabetes manager 104 and the other devices. The configurator can communicate with users through standard web or computer screens in non-web applications. The configurator transmits user-approved configurations to the devices of the diabetes management system 300. The analyzer retrieves data from the diabetes manager 104, stores the data in a database, and outputs analysis results through standard web pages or computer screens in non-web based applications.

The diabetes manager 104 can communicate with the mobile device 302 using Bluetooth. The mobile device 302 can include a cellular phone, a PDA, or a pager. The diabetes manager 104 can send messages to an external network through the mobile device 302. The mobile device 302 can transmit messages to the external network based on requests received from the diabetes manager 104.

In some embodiments, the communication between the diabetes manager 104 and the insulin pump 202 or 204 can be made more secure and reliable by including various security features. When the diabetes manager 104 and the insulin pump 202 or 204 will communicate wirelessly, for example, the diabetes manager 104 and the insulin pump 202 or 204 can be paired to establish a secure bidirectional communication link. Various exemplary methods of pairing a handheld diabetes managing device (such as diabetes manager 104) and an insulin pump (such as insulin pump 202 or 204) are illustrated in FIGS. 4-10.

Figure 4:
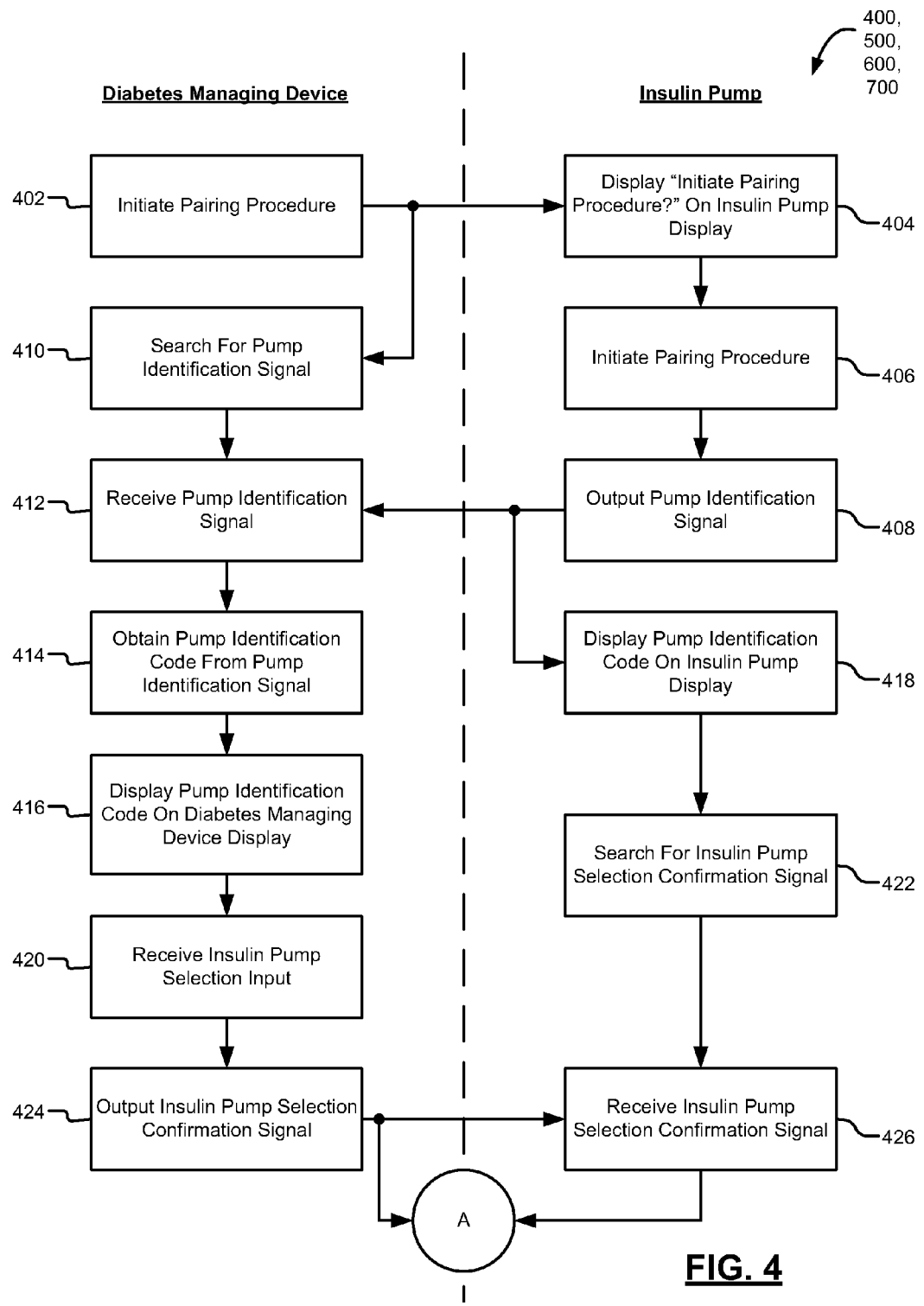
FIG. 4 shows a flow-chart illustrating a portion of an exemplary method of pairing a handheld diabetes managing device and an insulin pump according to the present disclosure.
Figure 5:
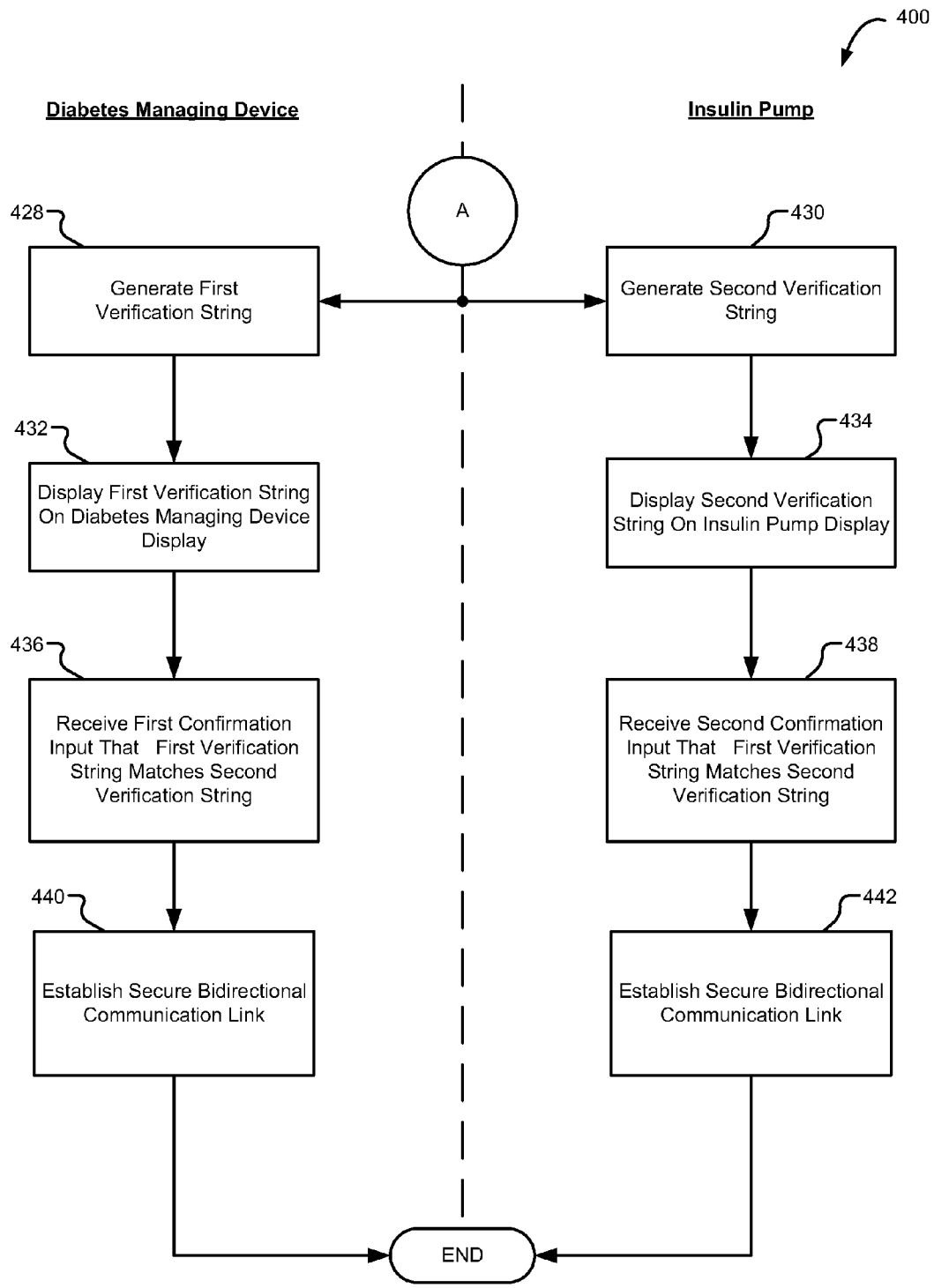
FIG. 5 shows a flow-chart illustrating a portion of an exemplary method of pairing a handheld diabetes managing device and an insulin pump according to the present disclosure.

Referring now to FIGS. 4 and 5, a first exemplary method 400 of pairing a handheld diabetes managing device and an insulin pump according to the present disclosure illustrated. While each step in the exemplary method 400 is illustrated and will be described herein as occurring at one of the handheld diabetes managing device or the insulin pump, one skilled in the art will appreciate that each step could occur at the other one, or both, of the handheld diabetes managing device or the insulin pump. For example only, method 400 begins at step 402 with the pairing procedure being initiated at the diabetes managing device and proceeds to step 404 with the insulin pump displaying "Initiate Pairing Procedure?" on an insulin pump display. One skilled in the art will recognize that the pairing procedure can instead be initiated at the insulin device and the diabetes managing device can display "Initiate Pairing Procedure?" on a diabetes managing device display.

Method 400 begins at step 402 with the pairing procedure being initiated at the diabetes managing device. The method proceeds to step 404 at which the insulin pump displays "Initiate Pairing Procedure?" on an insulin pump display. At step 406, the pairing procedure is initiated at the insulin pump. The pairing procedure can be initiated by placing the diabetes managing device and/or insulin pump in a "pairing" mode, for example, by a switch or push button. In some embodiments, a user, such as the patient 100 or clinician 102 described above, can initiate the pairing procedure, for example, by selecting an "Initiate Pairing Procedure?" option from a dropdown menu on the diabetes managing device and/or insulin pump or by choosing "Yes" or similar when prompted by "Initiate Pairing Procedure?" on the display. In some embodiments, the diabetes managing device display and/or the insulin pump display can be a touchscreen that allows a user to touch an appropriate location on the display to initiate the pairing procedure.

At step 410, the diabetes managing device searches for a pump identification signal, which is output from the insulin pump at step 408. The pump identification signal can include a pump identification code that contains information sufficient to uniquely identify the insulin pump, for example, the brand name, model and/or serial number. The diabetes managing device receives the pump identification signal at step 412 and obtains the pump identification code from the pump identification signal at step 414. The pump identification code can then be displayed on the diabetes managing device display (step 416). In some embodiments, the diabetes managing device can display information (such as a pump identification code) related to any and all insulin pumps that are within the communication range of the diabetes managing device.

In order to ensure that the proper pump identification code is selected, the insulin pump can display its unique pump identification code on its display (step 418). The user (patient 100, clinician 102, etc.) can then choose the pump identification code on the diabetes managing device that matches the pump identification code displayed on the insulin pump. In this manner, the proper pump identification code can be selected such that the diabetes managing device receives an insulin pump selection input at step 420. The insulin pump can search for an insulin pump selection confirmation signal (step 422), which is output from the diabetes managing device at step 424. At step 426, the insulin pump selection confirmation signal is received by the insulin pump to inform the insulin pump that it has been selected by the diabetes managing device for pairing.

The method 400 continues, as shown in FIG. 5, to steps 428 and 430 at which the diabetes managing device and insulin pump generate first and second verification strings, respectively. The first verification string can be displayed on the diabetes managing device display (step 432) and the second verification string can be displayed on the insulin pump display (step 434). If the first and second verification strings match, the diabetes managing device can receive a first confirmation input at step 436. Similarly, the insulin pump can receive a second confirmation input at step 438 if the first and second verification strings match.

In some embodiments, the user (patient 100, clinician 102, etc.) can confirm that first and second verification strings match and input the first and second confirmation inputs into the diabetes managing device and insulin pump, respectively. The user can input the first and second confirmation inputs, for example, by actuating a switch or push button, selecting an appropriate option from a dropdown menu on the diabetes managing device and/or insulin pump or by selecting "Match" or similar option on the diabetes managing device and/or insulin pump displays. In some embodiments, the diabetes managing device display and/or the insulin pump display can be touch screens that allows a user to touch an appropriate location on the display to input the first and second confirmation inputs. For example only, the diabetes managing device (diabetes manager 104) can have a touch screen display that displays the first verification string, a message reading "Does this code match the code on the insulin pump you are attempting to pair?" and two soft buttons—one reading "Yes" and the other "No." Similarly, the insulin pump can have a touch screen display that displays the second verification string, a message reading "Does this code match the code on the diabetes manager you are attempting to pair?" and two soft buttons—one reading "Yes" and the other "No." In this example, the user can input the first and second confirmation inputs into the diabetes managing device and insulin pump, respectively, by activating one of the soft buttons by touching the touch screen at the appropriate location.

Upon receipt of the first confirmation input at the diabetes managing device and the second confirmation input at the insulin pump, a secure bidirectional communication link is established at steps 440 and 442 to complete the pairing procedure, after which method 400 ends. If the first and second verification strings do not match, however, the pairing procedure can terminate (or be terminated by the user) without pairing the diabetes managing device and insulin pump.

In order to provide further security, the first and second verification strings can be independently generated by the diabetes managing device and insulin pump, respectively. In some embodiments, further described below, the first and second verification strings can be generated by an algorithm that is performed at each of the diabetes managing device and insulin pump. An input (for example, an encryption key) can be generated at one of the diabetes managing device and insulin pump and transmitted to the other one of the diabetes managing device and insulin pump. For example only, the input can be generated by a random number generator or similar device, or the input may be selected from a list of all possible inputs, e.g., based on output of a random number generator or similar. This input can be utilized by the algorithm to generate the first and second verification strings. In this manner, the first and second verification strings are not transmitted between the diabetes managing device and the insulin pump and, thus, are not subject to being intercepted and used to pair an unauthorized device with the diabetes managing device or insulin pump.

Figure 6:
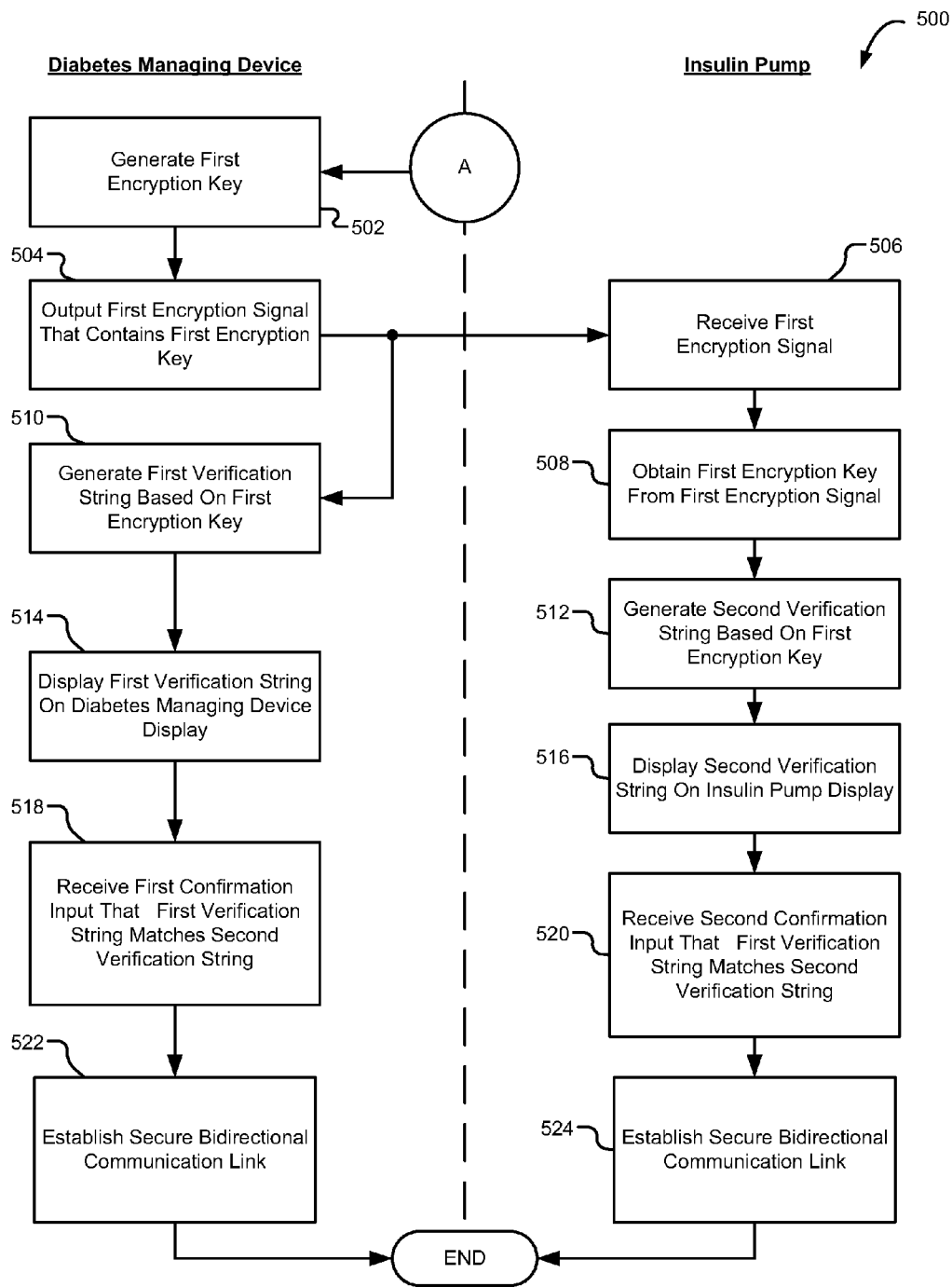
FIG. 6 shows a flow-chart illustrating a portion of an exemplary method of pairing a handheld diabetes managing device and an insulin pump according to the present disclosure.

Referring now to FIGS. 4 and 6, a second exemplary method 500 of pairing a handheld diabetes managing device and an insulin pump according to the present disclosure illustrated. Method 500 is similar to method 400 and can include one, more or all of steps 402 to 426 described above.

After the diabetes managing device outputs the insulin pump selection confirmation signal at step 424 and the insulin pump receives the insulin pump confirmation signal at step 426 (FIG. 4), method 500 proceeds to step 502 as shown in FIG. 6. At step 502 the diabetes managing device generates a first encryption key. For example only, the first encryption key can be a public RSA key that can be used with the RSA algorithm, a well-known public-key cryptography algorithm, however, it is possible that any type of encryption key can be utilized with the present disclosure. The diabetes managing device can then output a first encryption signal that contains the first encryption key at step 504. At step 506, the insulin pump can receive the first encryption signal and obtain the first encryption key from the first encryption signal at step 508.

Based on and utilizing the first encryption key, the diabetes managing device (step 510) and the insulin pump (step 512) can generate the first and second verification strings, respectively. As described above, the first encryption key can be input to or otherwise utilized by the algorithm stored at both the diabetes managing device and the insulin pump to independently generate the first and second verification strings. At step 514, the first verification string can be displayed on the diabetes managing device display. Similarly, at step 516 the second verification string can be displayed on the insulin pump display. If the first and second verification strings match, the diabetes managing device can receive a first confirmation input at step 518 and the insulin pump can receive a second confirmation input at step 520. In some embodiments, the user (patient 100, clinician 102, etc.) can confirm that first and second verification strings match and input the first and second confirmation inputs into the diabetes managing device and insulin pump, respectively.

Upon receipt of the first confirmation input at the diabetes managing device and the second confirmation input at the insulin pump, a secure bidirectional communication link is established at steps 522 and 524 to complete the pairing procedure, after which method 500 ends. If the first and second verification strings do not match, however, the pairing procedure can terminate (or be terminated by the user) without pairing the diabetes managing device and insulin pump.

Figure 7A:
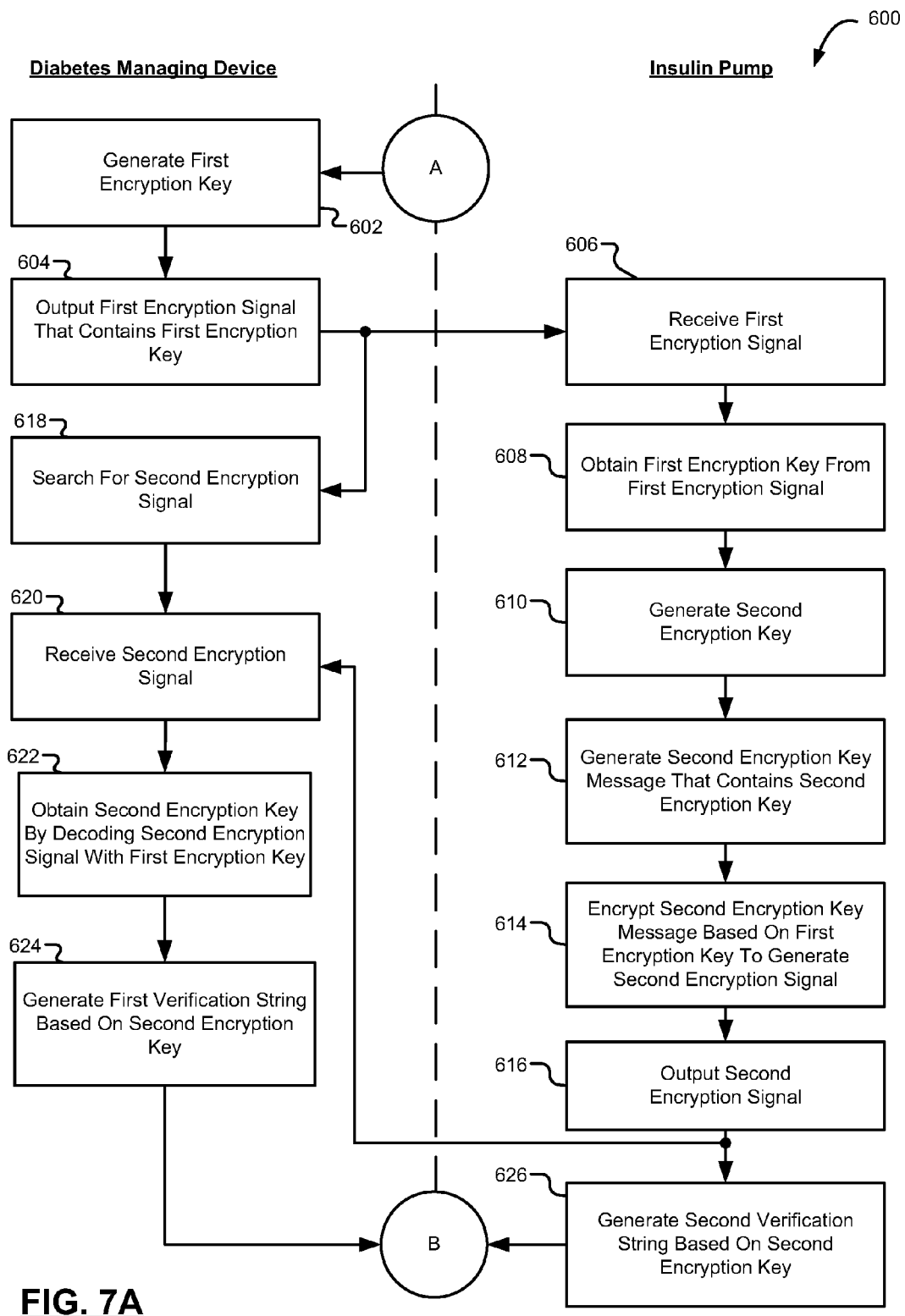
FIG. 7A shows a flow-chart illustrating a portion of an exemplary method of pairing a handheld diabetes managing device and an insulin pump according to the present disclosure.
Figure 7B:
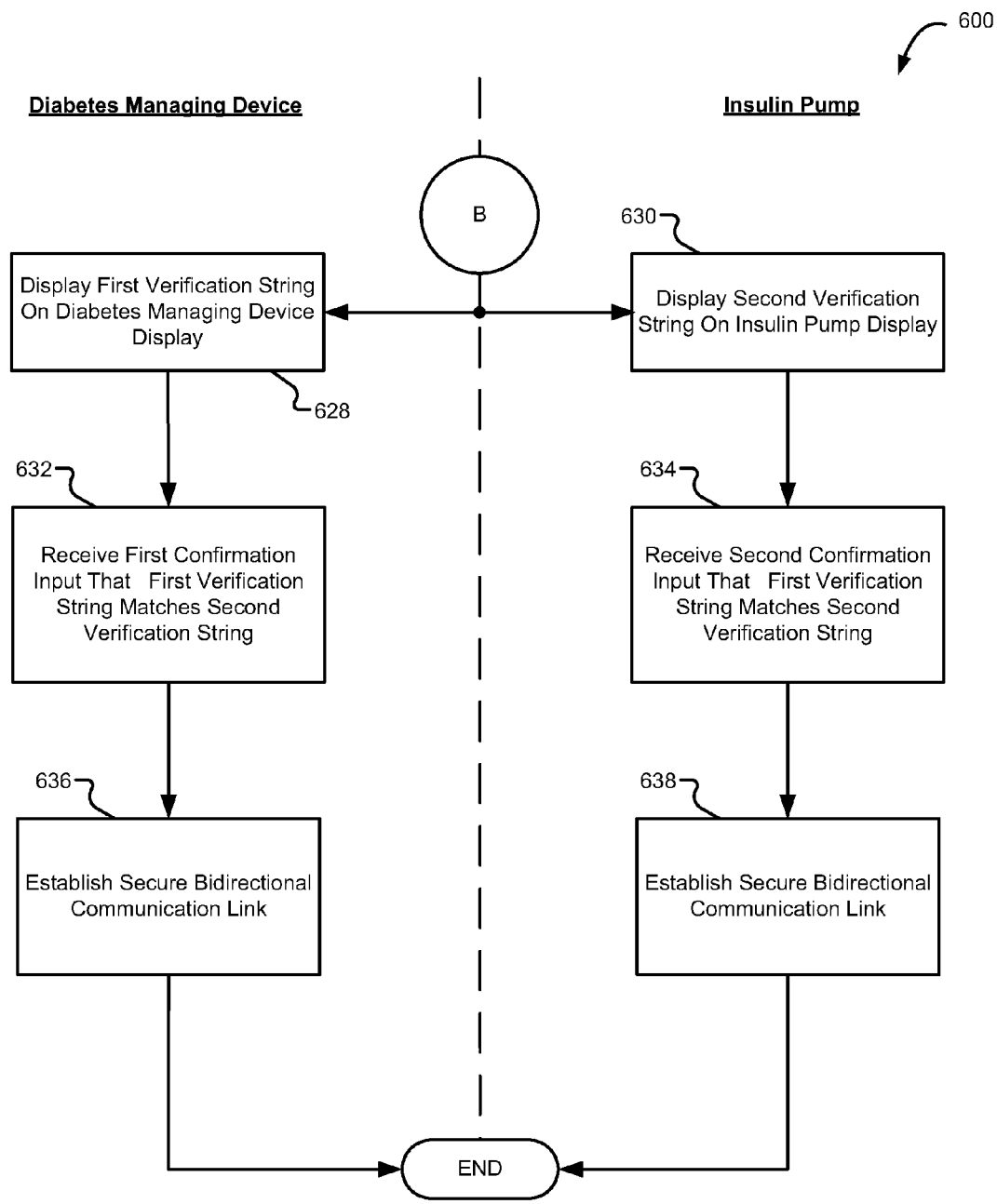
FIG. 7B shows a flow-chart illustrating a portion of an exemplary method of pairing a handheld diabetes managing device and an insulin pump according to the present disclosure.

Referring now to FIGS. 4, 7A and 7B, a third exemplary method 600 of pairing a handheld diabetes managing device and an insulin pump according to the present disclosure illustrated. Method 600 is similar to methods 400 and 500 and can include one, more or all of steps 402 to 426 described above.

After the diabetes managing device outputs the insulin pump selection confirmation signal at step 424 and the insulin pump receives the insulin pump confirmation signal at step 426 (FIG. 4), method 600 proceeds to step 602 as shown in FIG. 7A. At step 602 the diabetes managing device generates a first encryption key. For example only, the first encryption key can be a public RSA key that can be used with the RSA algorithm, a well-known public-key cryptography algorithm, however, it is possible that any type of encryption key can be utilized with the present disclosure. The diabetes managing device can then output a first encryption signal that contains the first encryption key at step 604. At step 606, the insulin pump can receive the first encryption signal and obtain the first encryption key from the first encryption signal at step 608.

After obtaining the first encryption key at step 608, the insulin pump can generate a second encryption key (step 610) and generate a second encryption key message that contains the second encryption key (step 612). For example only, the first and second encryption keys can each be a public RSA key, however, it is possible that any type of encryption key can be utilized with the present disclosure. At step 614, the insulin pump encrypts the second encryption key message (that includes the second encryption key) based on and utilizing the first encryption key to generate a second encryption signal. The insulin pump then outputs the second encryption signal at step 616.

After outputting the first encryption signal, the diabetes managing device can search for the second encryption signal at step 618. The diabetes managing device can receive the second encryption signal (step 620) and obtain the second encryption key from the second encryption signal (step 622). In various embodiments, the diabetes managing device can obtain the second encryption key by decoding the second encryption signal with the first encryption key, which was generated at step 602.

Based on and utilizing the second encryption key, the diabetes managing device (step 624) and the insulin pump (step 626) can generate the first and second verification strings, respectively. Similar to the process described above in regard to the first encryption key, the second encryption key can be input to or otherwise utilized by an algorithm stored at both the diabetes managing device and the insulin pump to independently generate the first and second verification strings. Referring now to FIG. 7B, the first verification string can be displayed on the diabetes managing device display at step 628. Similarly, at step 630 the second verification string can be displayed on the insulin pump display. If the first and second verification strings match, the diabetes managing device can receive a first confirmation input (step 632) and the insulin pump can receive a second confirmation input (step 634). In some embodiments, the user (patient 100, clinician 102, etc.) can confirm that first and second verification strings match and input the first and second confirmation inputs into the diabetes managing device and insulin pump, respectively.

Upon receipt of the first confirmation input at the diabetes managing device and the second confirmation input at the insulin pump, a secure bidirectional communication link is established at steps 636 and 638 to complete the pairing procedure, after which method 600 ends. If the first and second verification strings do not match, however, the pairing procedure can terminate (or be terminated by the user) without pairing the diabetes managing device and insulin pump.

Figure 8A:
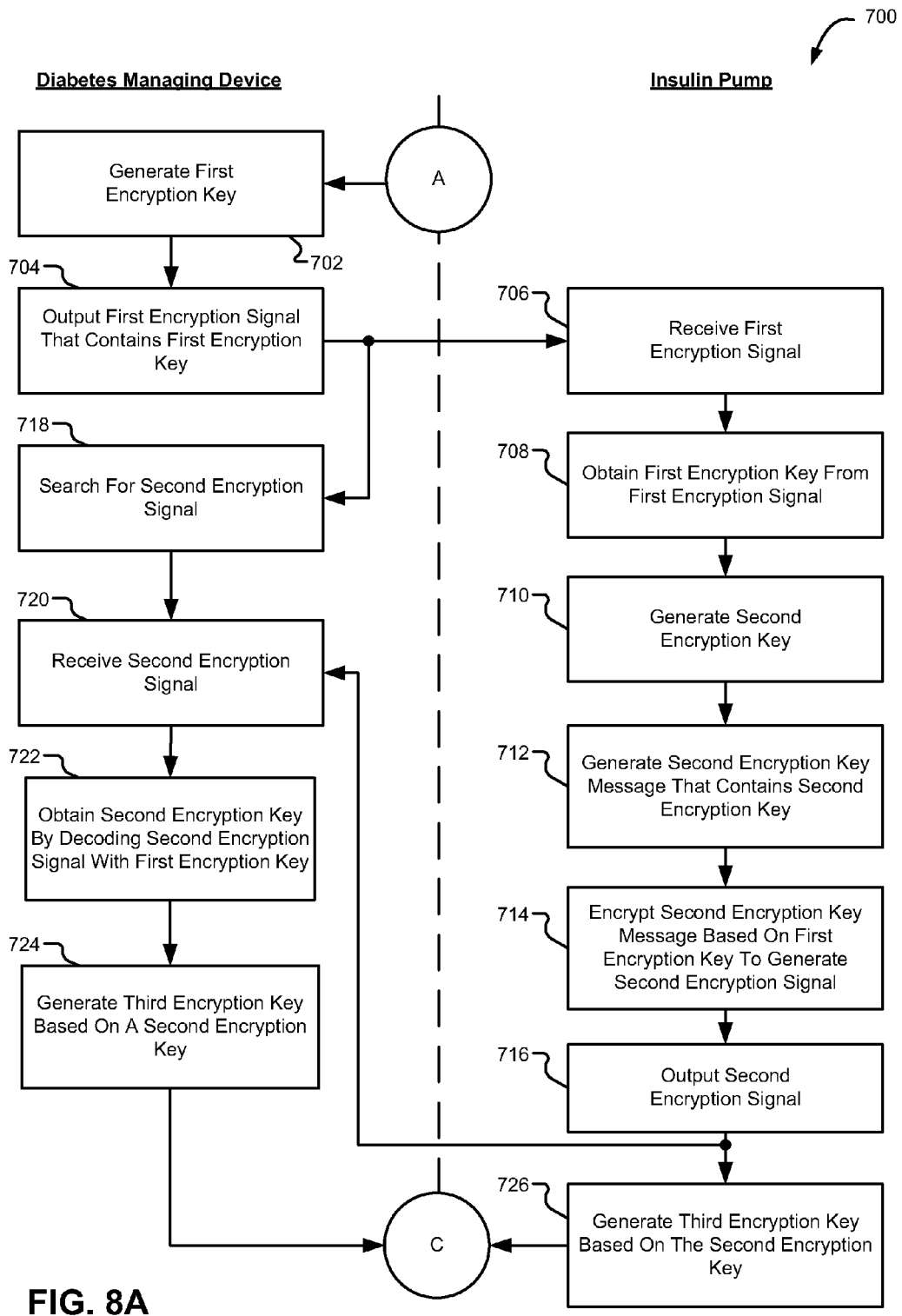
FIG. 8A shows a flow-chart illustrating a portion of an exemplary method of pairing a handheld diabetes managing device and an insulin pump according to the present disclosure.
Figure 8B:
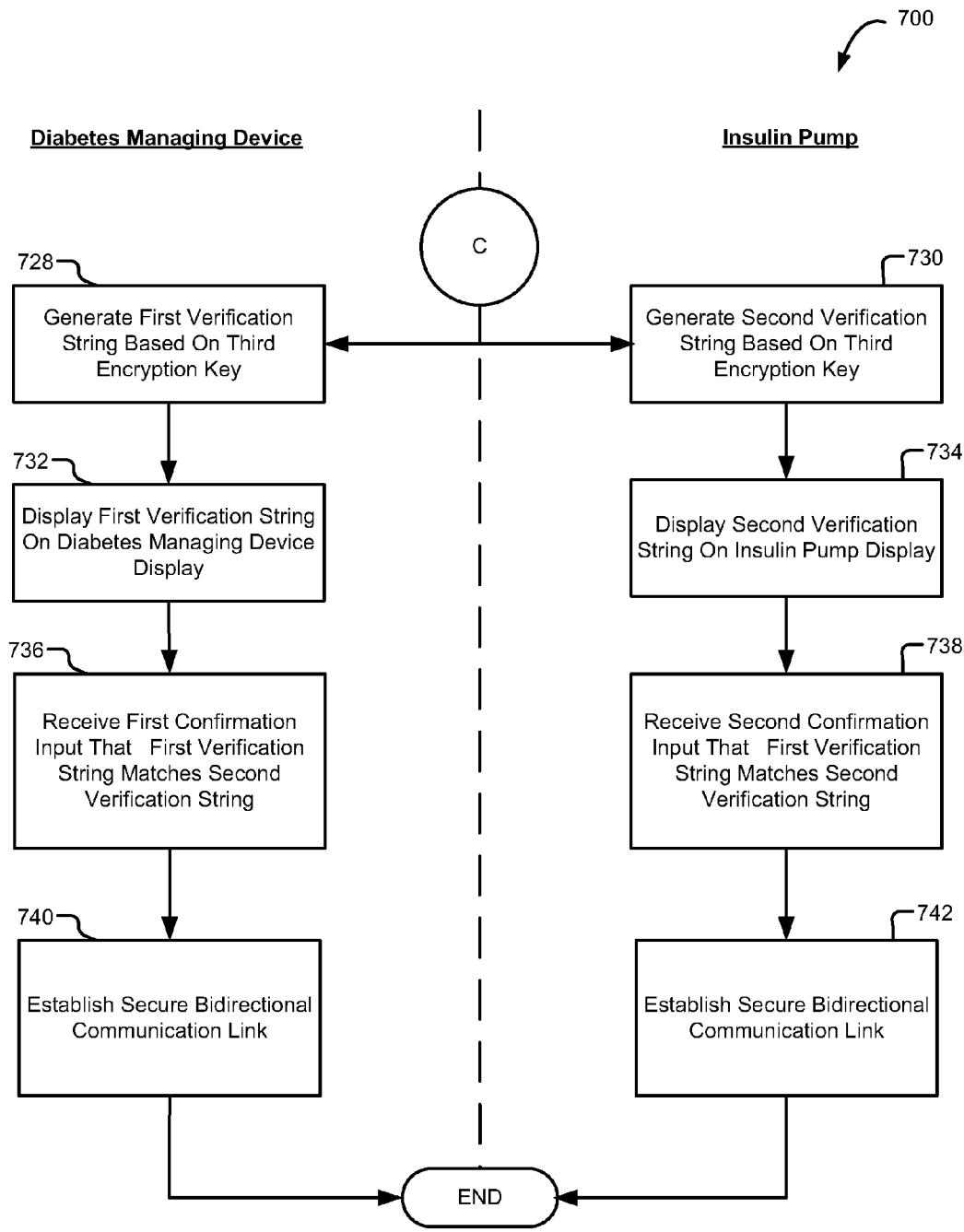
FIG. 8B shows a flow-chart illustrating a portion of an exemplary method of pairing a handheld diabetes managing device and an insulin pump according to the present disclosure.

Referring now to FIGS. 4, 8A and 8B, a fourth exemplary method 700 of pairing a handheld diabetes managing device and an insulin pump according to the present disclosure illustrated. Method 700 is similar to methods 400, 500 and 600 and can include one, more or all of steps 402 to 426 described above.

After the diabetes managing device outputs the insulin pump selection confirmation signal at step 424 and the insulin pump receives the insulin pump confirmation signal at step 426 (FIG. 4), method 700 proceeds to step 702 as shown in FIG. 8A. At step 702 the diabetes managing device generates a first encryption key. For example only, the first encryption key can be a public RSA key that can be used with the RSA algorithm, a well-known public-key cryptography algorithm, however, it is possible that any type of encryption key can be utilized with the present disclosure. The diabetes managing device can then output a first encryption signal that contains the first encryption key at step 704. At step 706, the insulin pump can receive the first encryption signal and obtain the first encryption key from the first encryption signal at step 708.

After obtaining the first encryption key at step 708, the insulin pump can generate a second encryption key (step 710) and generate a second encryption key message that contains the second encryption key (step 712). For example only, the first and second encryption keys can each be a public RSA key, however, it is possible that any type of encryption key can be utilized with the present disclosure. At step 714, the insulin pump encrypts the second encryption key message (that includes the second encryption key) based on and utilizing the first encryption key to generate a second encryption signal. The insulin pump then outputs the second encryption signal at step 716.

After outputting the first encryption signal, the diabetes managing device can search for the second encryption signal at step 718. The diabetes managing device can receive the second encryption signal (step 720) and obtain the second encryption key from the second encryption signal (step 722). In various embodiments, the diabetes managing device can obtain the second encryption key by decoding the second encryption signal with the first encryption key, which was generated at step 702.

Based on and utilizing the second encryption key, both the diabetes managing device (step 724) and the insulin pump (step 726) can generate a third encryption key. Similar to the process described above in regard to the generation of the first and second verification strings based on the second encryption key, the second encryption can be input to or otherwise utilized by an algorithm stored at both the diabetes managing device and the insulin pump to independently generate the third encryption key. For example only, the first encryption key can be a Twofish cipher key that can be used with the Twofish algorithm, a well-known cryptography algorithm.

Referring now to FIG. 8B, based on and utilizing the third encryption key, the diabetes managing device (step 728) and the insulin pump (step 730) can generate the first and second verification strings, respectively. Similar to the process described above in regard to the first and second encryption keys, the third encryption can be input to or otherwise utilized by the algorithm stored at both the diabetes managing device and the insulin pump to independently generate the first and second verification strings. The first verification string can be displayed on the diabetes managing device display at step 732. Similarly, at step 734 the second verification string can be displayed on the insulin pump display. If the first and second verification strings match, the diabetes managing device can receive a first confirmation input (step 736) and the insulin pump can receive a second confirmation input (step 738). In some embodiments, the user (patient 100, clinician 102, etc.) can confirm that first and second verification strings match and input the first and second confirmation inputs into the diabetes managing device and insulin pump, respectively.

Upon receipt of the first confirmation input at the diabetes managing device and the second confirmation input at the insulin pump, a secure bidirectional communication link is established at steps 740 and 742 to complete the pairing procedure, after which method 700 ends. If the first and second verification strings do not match, however, the pairing procedure can terminate (or be terminated by the user) without pairing the diabetes managing device and insulin pump.

Figure 9:
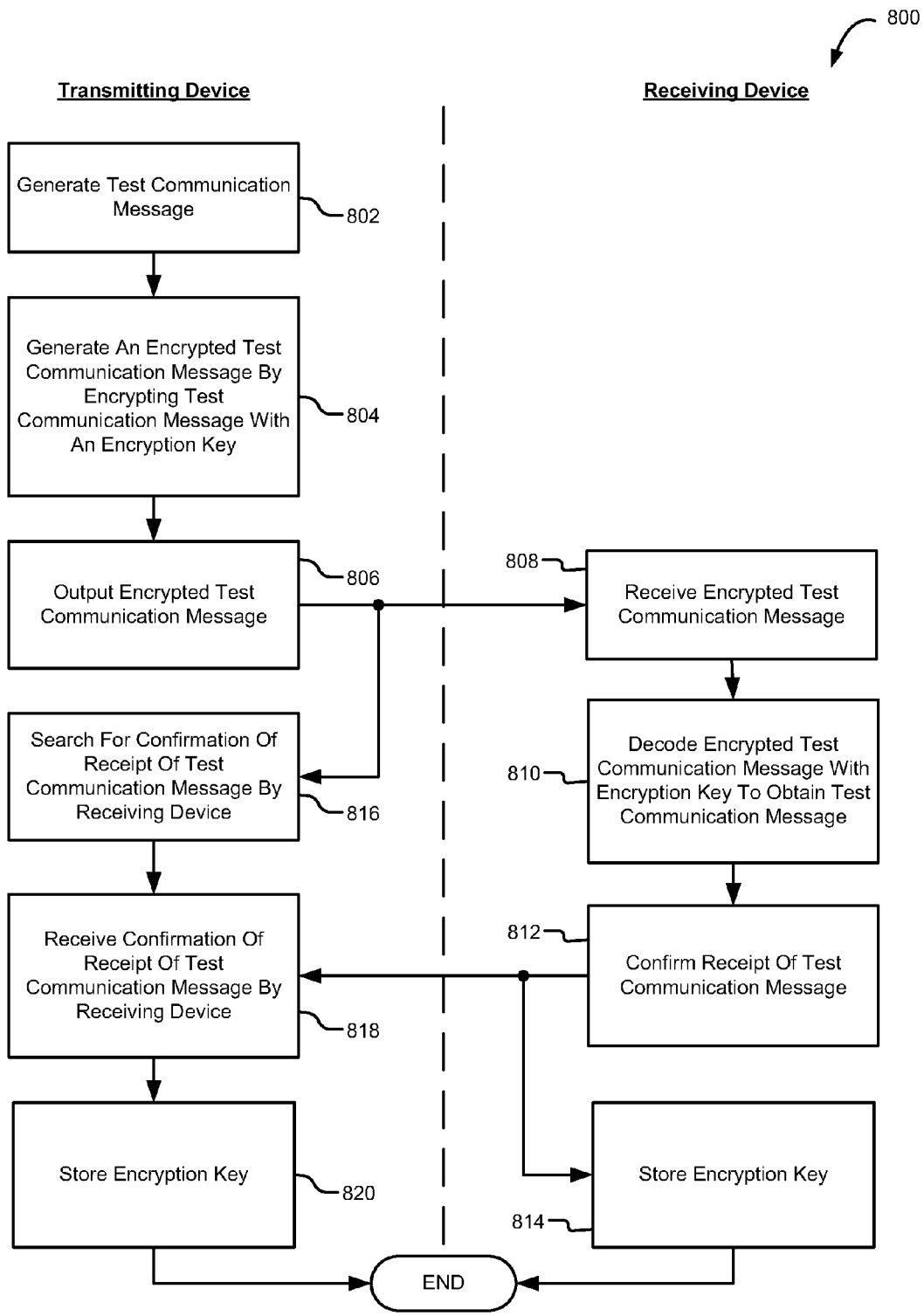
FIG. 9 shows a flow-chart illustrating an exemplary method of establishing a secure bidirectional communication link during pairing of a handheld diabetes managing device and an insulin pump according to the present disclosure.

Referring now to FIG. 9, an exemplary method 800 of establishing a secure bidirectional communication link during pairing of a handheld diabetes managing device and an insulin pump according to the present disclosure is illustrated. Method 800 can be utilized, for example, at steps 440, 442, 522, 524, 636, 638, 740 and 742 described above. In FIG. 9, method 800 is illustrated as taking place at a transmitting device and a receiving device. One skilled in the art will appreciate that the diabetes managing device (such as diabetes manager 104) and insulin pump (such as insulin pump 202 or 204) described above can act as either one of the transmitting device or the receiving device. That is, the diabetes managing device can act as the transmitting device and the insulin pump can act as the receiving device, or the insulin pump can act as the transmitting device and the diabetes managing device can act as the receiving device.

The method 800 begins at step 802 at which the transmitting device generates a test communication message. At step 804, the transmitting device then encrypts the test communication message with an encryption key to generate an encrypted test communication message. The encryption key can be any type of encryption key, including but not limited to the first, second or third encryption key described above. The encrypted test communication message is output by the transmitting device at step 806 and received by the receiving device at step 808. The receiving device then decodes the encrypted test communication message with the encryption key to obtain the test communication message (step 810). In various embodiments, the test communication message can be authenticated, as described below with reference to FIG. 11. The receiving device then confirms receipt of the test communication message (step 812) and stores the encryption key (step 814) for future use.

After outputting the encrypted test communication message, the transmitting device searches for confirmation of receipt of the test communication message by the receiving device (step 816). At step 818, the transmitting device receives confirmation of receipt of the test communication message by the receiving device. The encryption key is stored at the transmitting device for future use at step 820, after which method 800 ends.

Figure 10:
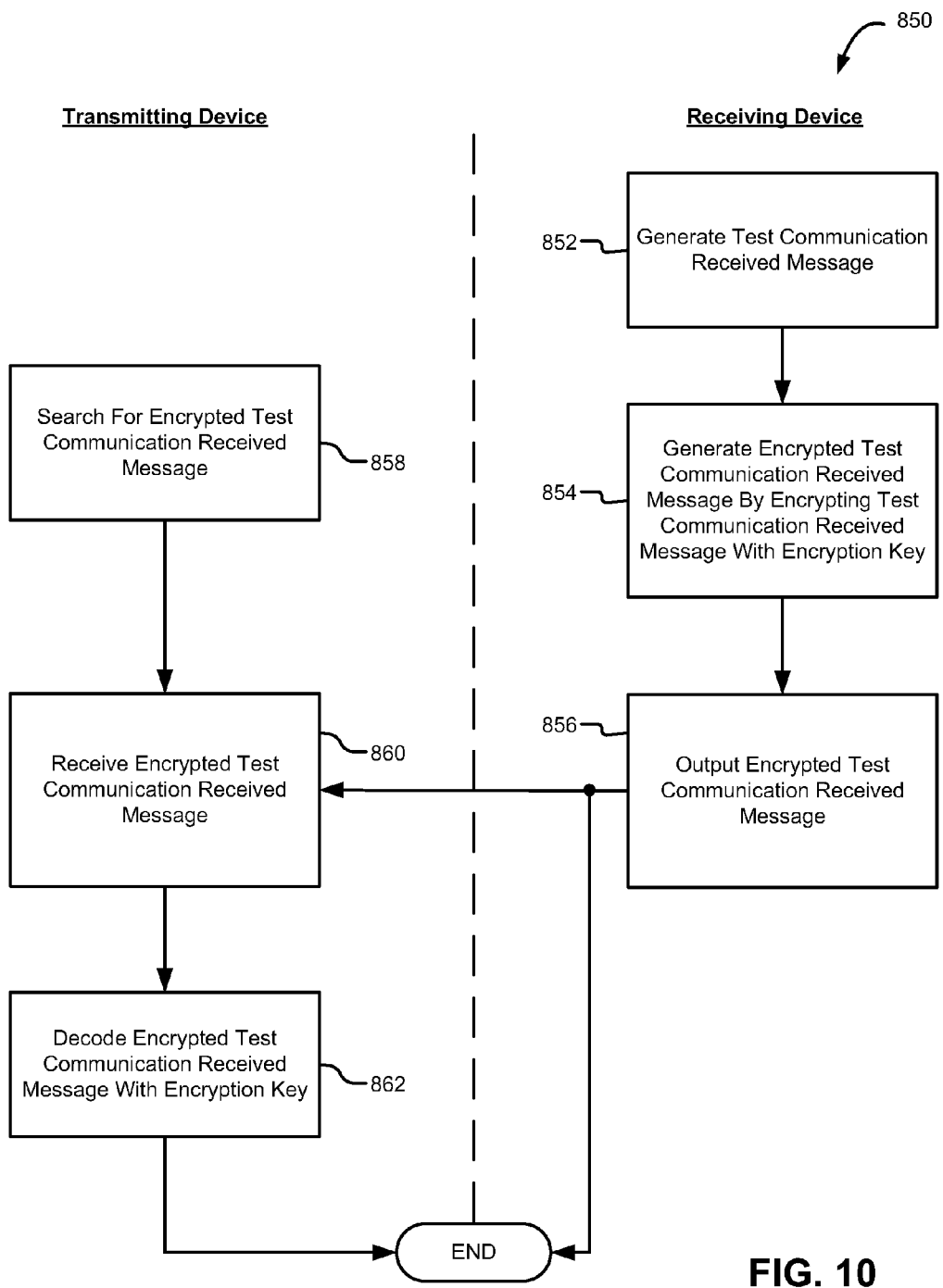
FIG. 10 shows a flow-chart illustrating an exemplary method of confirming receipt of a communication message by a receiving device according to the present disclosure.

Referring now to FIG. 10, an exemplary method 850 of confirming receipt of a test communication message by a receiving device according to the present disclosure illustrated. Method 850 can be utilized, for example, at step 812, 816 and 818 described above. In FIG. 10, method 850 is illustrated as taking place at a transmitting device and a receiving device. One skilled in the art will appreciate that the diabetes managing device (such as diabetes manager 104) and insulin pump (such as insulin pump 202 or 204) described above can act as either one of the transmitting device or the receiving device. That is, the diabetes managing device can act as the transmitting device and the insulin pump can act as the receiving device, or the insulin pump can act as the transmitting device and the diabetes managing device can act as the receiving device.

The method 850 begins at step 852 at which the receiving device generates a test communication received message. At step 854, the receiving device then encrypts the test communication received message with an encryption key to generate an encrypted test communication received message. The encryption key can be any type of encryption key, including but not limited to the first, second or third encryption key described above. The encrypted test communication received message is output by the received device at step 856.

At step 858, the transmitting device searches for the encrypted test communication received message output by the receiving device at step 856. The encrypted test communication received message is received by the transmitting device at step 860. The transmitting device then decodes the encrypted test communication received message with the encryption key at step 862, after which method 850 ends. While method 850 of FIG. 10 has been described in the context of confirming receipt of a test communication message by a receiving device, one skilled in the art will appreciate that method 850 can be utilized to confirm receipt of any, some or all communication messages sent between the transmitting and receiving devices.

Figure 11:
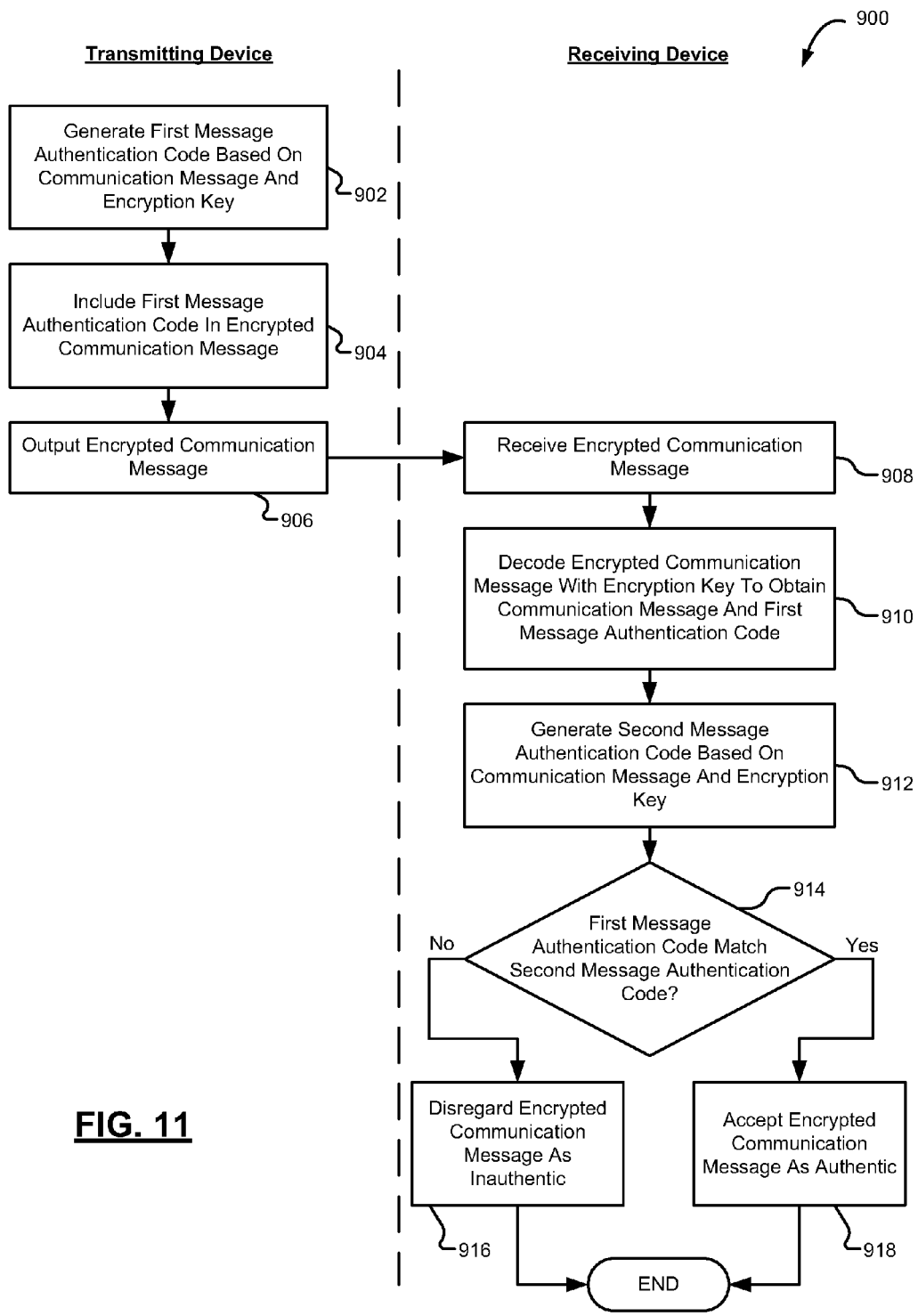
FIG. 11 shows a flow-chart illustrating an exemplary method of authenticating a communication message sent from a transmitting device to a receiving device according to the present disclosure.

Referring now to FIG. 11, an exemplary method 900 of authenticating a communication message sent from a transmitting device to a receiving device according to the present disclosure illustrated. Method 900 can be utilized, for example, to authenticate the test communication message described above in relation to FIGS. 9 and 10. In various embodiments, method 900 can be used to authenticate each and every communication message sent from the transmitting device to the receiving device.

In FIG. 11, method 900 is illustrated as taking place at a transmitting device and a receiving device. One skilled in the art will appreciate that the diabetes managing device (such as diabetes manager 104) and insulin pump (such as insulin pump 202 or 204) described above can act as either one of the transmitting device or the receiving device. That is, the diabetes managing device can act as the transmitting device and the insulin pump can act as the receiving device, or the insulin pump can act as the transmitting device and the diabetes managing device can act as the receiving device.

The method 900 begins at step 902 at which the transmitting device generates a first message authentication code based on the communication message and the encryption key. The first message authentication code can be generated by a process that is similar to the process described above in regard to the generation of the first and second verification strings. For example only, the first message authentication code can be generated based on inputting the communication message and the encryption key to an algorithm stored at both the diabetes managing device and the insulin pump. The encryption key can be any type of encryption key, including but not limited to the first, second or third encryption key described above. At step 904, the transmitting device includes the first message authentication code in an encrypted communication message. The encrypted communication message can include a version of the communication message that has been encrypted with the encryption key, as well as the first message authentication code generate at step 902. For example only, the encrypted communication message can include two separate data fields; the first data field can include the communication message that has been encrypted and the second data field can include the first message authentication code.

The transmitting device outputs the encrypted communication message at step 906, which is received by the receiving device at step 908. The receiving device decodes the encrypted communication message at step 910 to obtain the communication message and the first message authentication code. At step 912, the receiving device can generate a second message authentication code based on the communication message and encryption key. The second message authentication code can be generated by the same process used to generate the first message authentication code described above, i.e., the second message authentication code can be generated by inputting the communication message and the encryption key to the algorithm stored at both the diabetes managing device and the insulin pump. If the diabetes managing device and the insulin pump both share the same algorithm and encryption key, each communication message may be authenticated by comparing the first and second message authentication codes. Thus, the receiving device compares the first and second message authentication codes at step 914. If the first and second message authentication codes do not match, the method 900 proceeds to step 916 at which the receiving device disregards the encrypted communication message as inauthentic. If, however, the first and second message authentication codes do match, the method 900 proceeds to step 918 at which the receiving device accepts the encrypted communication message as authentic. After either step 916 or 918, method 900 ends.

Figure 12:
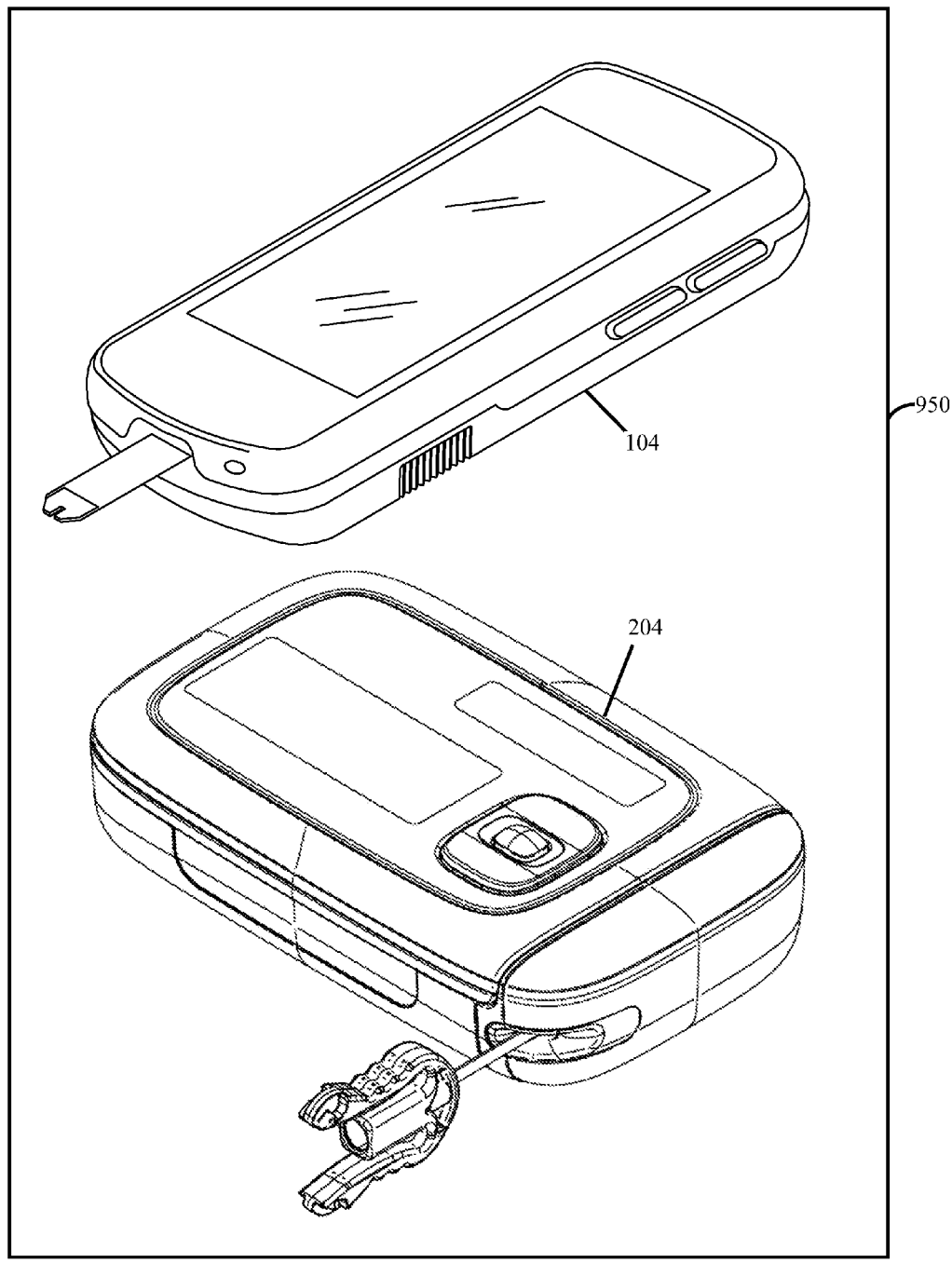
FIG. 12 shows an exemplary diabetes care kit for providing diagnostics and therapy according to the present disclosure.
Figure 13:
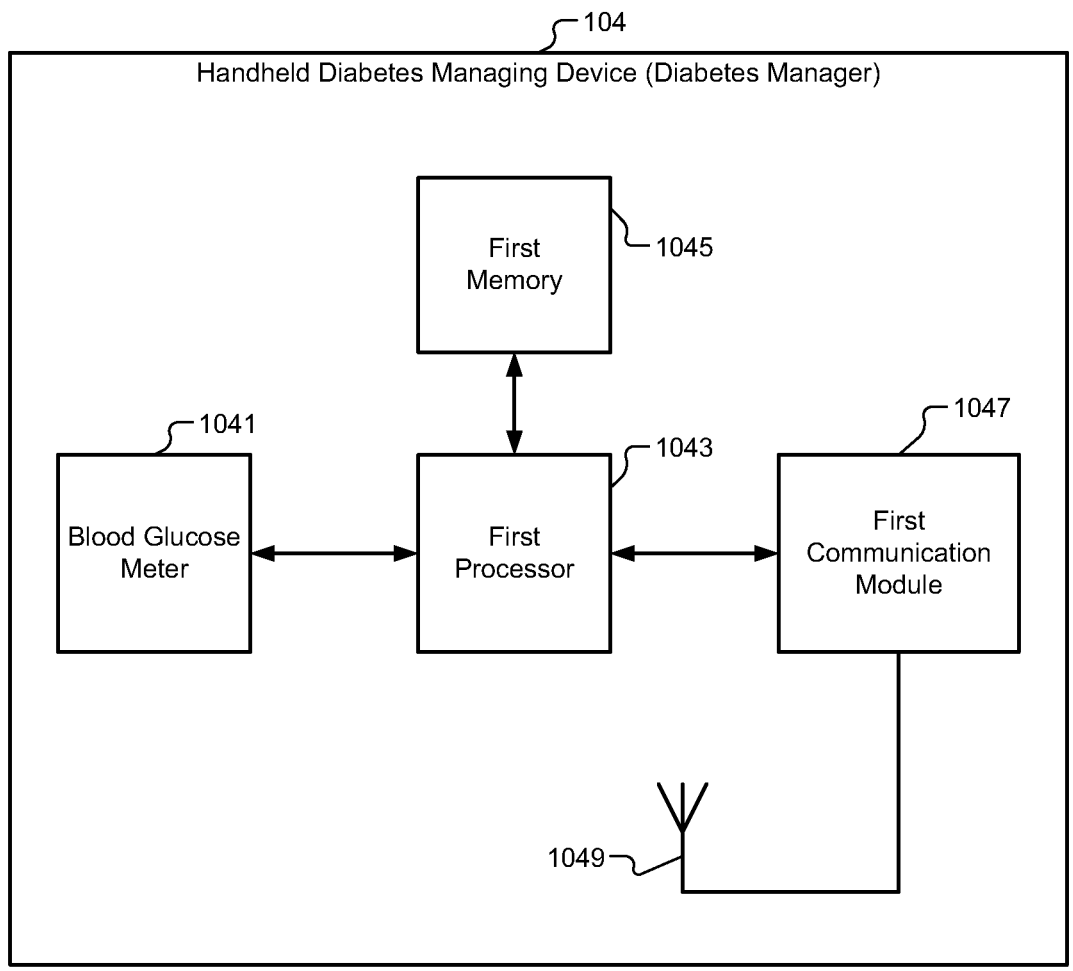
FIG. 13 shows a block diagram of an exemplary handheld diabetes managing device according to the present disclosure.
Figure 14:
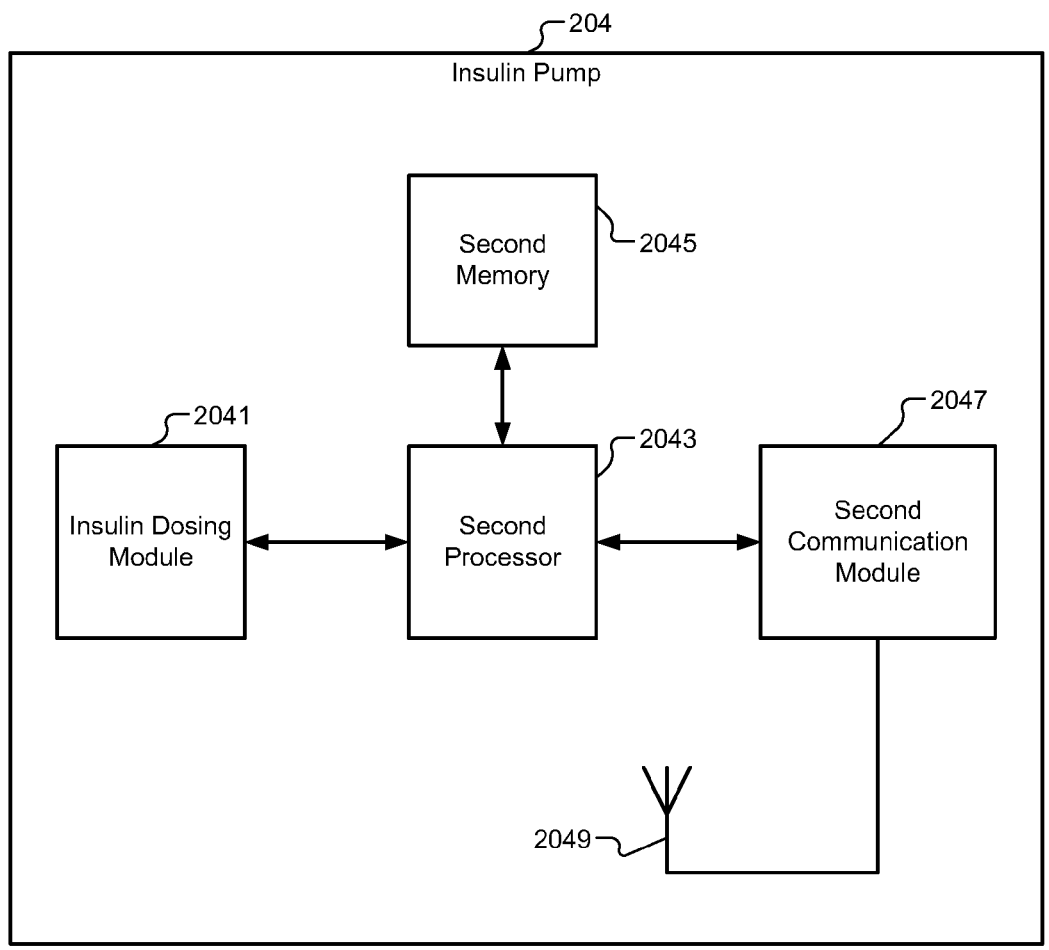
FIG. 14 shows a block diagram of an exemplary insulin pump according to the present disclosure.

Referring now to FIGS. 12-14, a diabetes care kit 950 for providing diagnostics and therapy according to the present disclosure is illustrated. Diabetes care kit 950 can include a handheld diabetes managing device (such as diabetes manager 104) and an insulin pump (such as insulin pump 202 or 204). Diabetes care kit 950 can be preconfigured to reduce initial setup by a user (patient 100, clinician 102, etc.), for example, by establishing a paired relationship between the diabetes manager 104 and insulin pump 204 before providing the diabetes care kit 950 to the user.

Referring now to FIG. 13, diabetes manager 104 can include a blood glucose meter 1041, a first processor 1043, a first memory 1045, a first communication module 1047 and a first antenna 1049. The blood glucose meter 1041 can determine a blood glucose level of a user, for example, by measuring the blood glucose in a capillary blood sample provided by the user or obtaining a blood glucose estimate provided by a continuous glucose monitor, such as CGM 200 described above. The blood glucose meter 1041 can be coupled to the first processor 1043 such that the first processor 1043 can receive the blood glucose level from the blood glucose meter 1041. Based on the blood glucose level, the first processor 1043 can generate an insulin pump command. The insulin pump command can be an instruction that notifies the insulin pump 204 to provide an appropriate dose of insulin to provide to the user. The first processor 1043 can generate the insulin pump command based on an algorithm stored in the first memory 1045. In addition to the blood glucose level of the user, the insulin pump command can be based on a number of other factors, such as the weight and insulin resistance of the user, and input(s) by the user regarding whether the user will be eating a meal or exercising.

An encryption key can also be preloaded into the first memory 1045 for use by the first processor 1043 and first communication module 1047. For example only, the encryption key can be loaded into the first memory 1045 during manufacture of the diabetes manager 104, after completion of manufacture but before the diabetes manager 104 is packaged or otherwise included in the kit 950, or any time before providing the kit 950 to a user. The encryption key (such as the first, second or third encryption key described above) can be utilized to establish a secure bidirectional communication link between the diabetes manager 104 and insulin pump 204 as well as for other security purposes (such as authentication of messages transmitted between the diabetes manager 104 and insulin pump 204), as described above.

The first communication module 1047 can be coupled to the first processor 1043 and first memory 1047. The first communication module 1047 can utilize the encryption key to generate encrypted communication messages, such as an encrypted communication message based on the insulin pump command. The first antenna 1049 can be coupled to the first communication module 1047 such that encrypted communication messages can be transmitted from the first antenna 1049 to, e.g., the insulin pump 204.

Referring now to FIG. 14, insulin pump 204 can include an insulin dosing module 2041, a second processor 2043, a second memory 2045, a second communication module 2047 and a second antenna 2049. The insulin dosing module 2041 can dispense insulin to a user (patient 100) based on the insulin pump command. The insulin dosing module 2041 can be coupled to the second processor 2043 such that the second processor 1043 can transmit an insulin dose command to the insulin dosing module 2041. The insulin dose command can be generated by the second processor 2043 based on the insulin pump command. An algorithm stored in the second memory 2045 can be utilized by the processor 2043 to generate the insulin dose command. In addition to the insulin pump command, the insulin dose command can be based on a number of other factors, such as a previous dose or doses provided to the user or a blood glucose estimate provided by a continuous glucose monitor, such as CGM 200 described above.

The encryption key can also be preloaded into the second memory 2045 for use by the second processor 2043 and second communication module 2047. For example only, the encryption key can be loaded into the second memory 2045 during manufacture of the insulin pump 204, after completion of manufacture but before the insulin pump 204 is packaged or otherwise included in the kit 950, or any time before providing the kit 950 to a user. The encryption key (such as the first, second or third encryption key described above) can be utilized to establish a secure bidirectional communication link between the diabetes manager 104 and insulin pump 204 as well as for other security purposes (such as authentication of messages transmitted between the diabetes manager 104 and insulin pump 204), as described above.

The second antenna 2049 can be coupled to the second communication module 2047. The second antenna 2049 can decode encrypted communication messages sent by the diabetes manager 104, such as the encrypted communication message based on the insulin pump command. The second communication module 2047 can be coupled to the second antenna 2049, as well as the second processor 2043 and second memory 2047. The second communication module 2047 can utilize the encryption key to decode the encrypted communication messages sent by the diabetes manager 104. For example, the second communication module 1047 can utilize the encryption key to decode the encrypted communication message to obtain the insulin pump command generated by the diabetes manager 104.

While the diabetes manager 104 has been described above as generating and transmitting encrypted communication messages to the insulin pump 204, and the insulin pump has been described as receiving and decoding encrypted communication messages from the diabetes manager 104, one skilled in the art will appreciate that the diabetes manager 104 can also receive and decode encrypted communication messages generated by and transmitted from the insulin pump 204.

Furthermore, the kit 950 and its associated diabetes manager 104 and insulin pump 204 can perform the methods described above in relation to FIGS. 4-11, such as, but not limited to, any or all of the methods 400, 500, 600, 700, 850, 900 for pairing and utilizing a secure bidirectional communication link between the diabetes manager 104 and insulin pump 204, any or all of the methods 800, 850 for establishing the secure bidirectional communication link by sending a test communication message from the diabetes manager 104 to the insulin pump 204 (or vice-versa) and confirming receipt of communication messages sent from the diabetes manager 104 to the insulin pump 204 (or vice-versa), and the method 900 of method of authenticating a communication message sent from the diabetes manager 104 to the insulin pump 204 (or vice-versa). For example, the kit 950 and its associated diabetes manager 104 and insulin pump 204 can perform the methods of pairing and utilizing a secure bidirectional communication link, as described above, in the event that a user replaces a component of, or adds a component (such as, CGM 200) to, the kit 950 after obtaining the kit 950.

In some exemplary embodiments, the handheld diabetes managing device (diabetes manager 104) can include a first pairing application. The first pairing application can be implemented as computer executable instructions stored on a non-transitory tangible computer readable medium at the handheld diabetes managing device, such as first memory 1045. The first pairing application can be configured to execute a pairing procedure at the handheld diabetes managing device (diabetes manager 104) for pairing the handheld diabetes managing device (diabetes manager 104) and the insulin pump (insulin pump 204). Similarly, the insulin pump (insulin pump 204) can include a second pairing application. The second pairing application can be implemented as computer executable instructions stored on a non-transitory tangible computer readable medium at the insulin pump, such as second memory 2045. The second pairing application can be configured to execute the pairing procedure at the insulin pump (insulin pump 204). The pairing procedure can include, for example, any or all of the methods 400, 500, 600, 700, 800, 850, 900 for pairing and utilizing a secure bidirectional communication link between the diabetes manager 104 and insulin pump 204 that are described above.

In some exemplary embodiments, the handheld diabetes managing device (diabetes manager 104) can include a first message confirmation application. The first message confirmation application can be implemented as computer executable instructions stored on a non-transitory tangible computer readable medium at the handheld diabetes managing device, such as first memory 1045. The first message confirmation application can be configured to execute a procedure at the handheld diabetes managing device (diabetes manager 104) for confirming receipt of a communication message at a receiving device, such as the handheld diabetes managing device (diabetes manager 104) and/or the insulin pump (insulin pump 204). Similarly, the insulin pump (insulin pump 204) can include a second message confirmation application. The second message confirmation application can be implemented as computer executable instructions stored on a non-transitory tangible computer readable medium at the insulin pump, such as second memory 2045. The second message confirmation application can be configured to execute the procedure for confirming receipt of the communication message at the receiving device at the insulin pump (insulin pump 204). The procedure can include, for example, any or all of the methods 800, 850 for confirming receipt of the communication message at the diabetes manager 104 and/or insulin pump 204 that are described above.

Finally, in various exemplary embodiments, the handheld diabetes managing device (diabetes manager 104) can include a first message authentication application. The first message authentication application can be implemented as computer executable instructions stored on a non-transitory tangible computer readable medium at the handheld diabetes managing device, such as first memory 1045. The first message authentication application can be configured to execute a procedure at the handheld diabetes managing device (diabetes manager 104) for authenticating a communication message received by a receiving device, such as the handheld diabetes managing device (diabetes manager 104) and/or the insulin pump (insulin pump 204). Similarly, the insulin pump (insulin pump 204) can include a second message authentication application. The second message authentication application can be implemented as computer executable instructions stored on a non-transitory tangible computer readable medium at the insulin pump, such as second memory 2045. The second message authentication application can be configured to execute the procedure for authenticating a communication message received by the receiving device. The procedure can include, for example, the method 900 for authenticating a communication message received by the diabetes manager 104 and/or insulin pump 204 that are described above.

The broad teachings of the disclosure can be implemented in a variety of forms. Therefore, while this disclosure includes particular examples, the true scope of the disclosure should not be so limited since other modifications will become apparent to the skilled practitioner upon a study of the drawings, the specification, and the following claims.

This detailed description is merely illustrative in nature and is in no way intended to limit the disclosure, its application, or uses. For purposes of clarity, the same reference numbers are used in the drawings to identify similar elements. As used herein, the phrase at least one of A, B, and C should be construed to mean a logical (A or B or C), using a non-exclusive logical or. It should be understood that steps within a method can be executed in different order without altering the principles of the present disclosure.

As used herein, the term module can refer to, be part of, or include an Application Specific Integrated Circuit (ASIC); an electronic circuit; a combinational logic circuit; a field programmable gate array (FPGA); a processor (shared, dedicated, or group) that executes code; other suitable components that provide the described functionality; or a combination of some or all of the above, such as in a system-on-chip. The term module can include memory (shared, dedicated, or group) that stores code executed by the processor.

The term code, as used above, can include software, firmware, and/or microcode, and can refer to programs, routines, functions, classes, and/or objects. The term shared, as used above, means that some or all code from multiple modules can be executed using a single (shared) processor. In addition, some or all code from multiple modules can be stored by a single (shared) memory. The term group, as used above, means that some or all code from a single module can be executed using a group of processors. In addition, some or all code from a single module can be stored using a group of memories.

The apparatuses and methods described herein can be implemented by one or more computer programs or applications executed by one or more processors. The computer programs and applications can include processor-executable instructions that are stored on a non-transitory tangible computer readable medium. The computer programs can also include stored data. Non-limiting examples of the non-transitory tangible computer readable medium are nonvolatile memory, magnetic storage, and optical storage.

What is claimed is:

1. A method for pairing a diabetes managing device with an insulin pump for secure wireless communication, comprising:

preloading an encryption key into a first memory of the diabetes managing device during manufacture of the diabetes managing device;

preloading the encryption key into a second memory of the insulin pump during manufacture of the insulin pump;

at the diabetes managing device, generating a first verification string from the encryption key;

at the insulin pump, generating a second verification string from the encryption key;

at the diabetes managing device, displaying the first verification string on a display of the diabetes managing device;

at the insulin pump, displaying the second verification string on a display of the insulin pump;

at the diabetes managing device, receiving a first confirmation input in response to the first verification string being displayed, the first confirmation input indicating that first verification string matches the second verification string;

at the insulin pump, receiving a second confirmation input in response to the second verification string being displayed, the second confirmation input indicating that the first verification string matches the second verification string; and establishing a secure bidirectional communication link between the diabetes managing device and the insulin pump based on the receipt of either the first confirmation input by the diabetes managing device or the receipt of the second confirmation input by the insulin pump.

2. The method of claim 1 further comprising:

at the insulin pump, outputting a pump identification signal that contains a pump identification code that uniquely identifies the insulin pump prior to generating the second verification string;

at the diabetes managing device, receiving the pump identification signal;

at the diabetes managing device, obtaining the pump identification code from the pump identification signal;

at the diabetes managing device, displaying the pump identification code on the display of the diabetes managing device;

at the insulin pump, displaying the pump identification code on the display of the insulin pump; and at the diabetes managing device, receiving an insulin pump selection input that selects the pump identification code corresponding to the insulin pump.

3. The method of claim 1 further comprises receiving the first confirmation input from a user of the diabetes managing device.

4. The method of claim 1 further comprises receiving the second confirmation input from a user of the insulin pump.

5. The method of claim 1 wherein the encryption key is further defined as an RSA key.

6. A system for providing diagnostics and therapy that is preconfigured to reduce initial setup by a user, comprising:
a handheld diabetes managing device including:
a blood glucose meter configured to determine a blood glucose level of a user,
a first processor coupled to the blood glucose meter and configured to generate an insulin pump command based on the blood glucose level,
a first memory coupled to the processor and preloaded with an encryption key,
a first pairing application implemented as computer executable instructions in the first memory, the first pairing application being configured to execute a pairing procedure at the handheld diabetes managing device,
a first communication processor coupled to the first processor and first memory and configured to generate an encrypted communication message based on the insulin pump command and the encryption key, and
a first antenna coupled to the first communication module and configured to transmit the encrypted communication message; and
an insulin pump including:
an infusion set configured to dispense insulin based on an insulin dose command,
a second processor coupled to the insulin dosing module and configured to generate the insulin dose command based on the insulin pump command,
a second memory coupled to the second processor and preloaded with the encryption key,
a second pairing application implemented as computer executable instructions in the second memory, the second pairing application being configured to execute the pairing procedure at the insulin pump,
a second communication processor coupled to the second processor and the second memory and configured to decrypt the encrypted communication message based on the encryption key to obtain the insulin pump command, and
a second antenna coupled to the second communication module and configured to receive the encrypted communication message,
wherein the handheld diabetes managing device and the insulin pump are paired using the pairing procedure such that a secure bidirectional communication link exists between the handheld diabetes managing device and the insulin pump, the pairing procedure including:
at the handheld diabetes managing device, generating a first verification string from the encryption key;
at the insulin pump, generating a second verification string from the encryption key;
at the handheld diabetes managing device, displaying the first verification string on a display of the diabetes managing device;
at the insulin pump, displaying the second verification string on a display of the insulin pump;
at the handheld diabetes managing device, receiving a first confirmation input in response to the first verification string being displayed in the handheld diabetes managing device;
at the insulin pump, receiving a second confirmation input in response to the second verification string being displayed on the insulin pump; and
establishing a secure bidirectional communication link between the handheld diabetes managing device and the insulin pump based on the receipt of either the first confirmation input at the handheld diabetes managing device or the second confirmation input at the insulin pump.

7. The system of claim 6 wherein the handheld diabetes managing device and the insulin pump are configured to communicate by transmitting messages that are encrypted based on the encryption key.

8. The system of claim 6 wherein the encryption key is an RSA public key.

9. The system of claim of claim 6 wherein the pairing procedure further comprises:
at the handheld diabetes managing device, generating a test communication message;
at the handheld diabetes managing device, generating an encrypted test communication message by encrypting the test communication message with the encryption key;
at the handheld diabetes managing device, outputting the encrypted test communication message;
at the insulin pump, receiving the encrypted test communication message;
at the insulin pump, decrypting the encrypted test communication message with the encryption key to obtain the test communication message; and
at the insulin pump, confirming receipt of the test communication message by the insulin pump.

10. The system of claim 9 wherein the handheld diabetes managing device further comprises a first message confirmation application implemented as computer executable instructions in the first memory and the insulin pump further comprises a second confirmation message application implemented as computer executable instructions in the second memory, wherein:
the second message confirmation application is configured to execute a third procedure at the insulin pump for confirming receipt of the test communication message at the insulin pump, the third procedure including:
generating a test communication received message,
generating an encrypted test communication received message by encrypting the test communication received message with the encryption key, and
outputting the encrypted test communication received message; and
the first message confirmation application is configured to execute a fourth procedure at the handheld diabetes managing device for confirming receipt of the test communication message at the insulin pump, the fourth procedure including:
receiving the encrypted test communication received message, and
decoding the encrypted test communication received message with the encryption key.

* * * * *